(12) United States Patent
Kim et al.

(10) Patent No.: US 9,913,670 B2
(45) Date of Patent: Mar. 13, 2018

(54) ROD INSERTER FOR FIXING OF PEDICLE SCREW, SCREW HOLDER WITH JOINT FOR MINIMAL INVASIVE SURGERY, SCREW REDUCER FOR MINIMAL INVASIVE SURGERY AND APPARATUS FOR MINIMAL INVASIVE SURGERY USING THESE DEVICES

(71) Applicant: Mantiz Logitech Co., Ltd., Daegu (KR)

(72) Inventors: Hyeun Sung Kim, Seoul (KR); Dong Hwa Heo, Seoul (KR); Hong won Yoon, Yongin-si (KR)

(73) Assignee: Mantiz Logitech Co., Ltd., Daegu (KR)

( * ) Notice: Subject to any disclaimer, the term of this patent is extended or adjusted under 35 U.S.C. 154(b) by 0 days.

(21) Appl. No.: 15/252,758

(22) Filed: Aug. 31, 2016

(65) Prior Publication Data

US 2017/0056076 A1 Mar. 2, 2017

(30) Foreign Application Priority Data

Aug. 31, 2015 (KR) .................. 10-2015-0122344
Aug. 31, 2015 (KR) .................. 10-2015-0122345
Aug. 31, 2015 (KR) .................. 10-2015-0122346

(51) Int. Cl.
*A61B 17/70* (2006.01)
*A61B 17/68* (2006.01)
*A61B 17/56* (2006.01)

(52) U.S. Cl.
CPC ........ *A61B 17/7086* (2013.01); *A61B 17/708* (2013.01); *A61B 2017/567* (2013.01); *A61B 2017/681* (2013.01)

(58) Field of Classification Search
CPC combination set(s) only.
See application file for complete search history.

(56) References Cited

U.S. PATENT DOCUMENTS 7,695,475 B2 * 4/2010 Justis ................. A61B 17/7089
606/250
7,918,878 B2 * 4/2011 Songer ............... A61B 17/7002
606/279

(Continued)

FOREIGN PATENT DOCUMENTS

KR         10-0623441 B1    9/2006
KR     10-2008-0004444 A    1/2008
(Continued)

*Primary Examiner* — Jan Christopher Merene
(74) *Attorney, Agent, or Firm* — Novick, Kim & Lee, PLLC; Jae Youn Kim

(57) ABSTRACT

Provided are a rod inserter for fixing a pedicle screw. The rod inserter for fixing a pedicle screw, the rod inserter including a rotational support unit having a length corresponding to a radius of lordosis formed by lumbar of vertebrae of a subject person and of which a lower end is fixed and a rotational insertion unit having a length corresponding to the radius and having one end rotatably coupled to an upper end of the rotational support unit and the other end to which an arc-shaped rod is detachably coupled. Thus, the arc-shaped rods having lengths shapes different from each other according to the number of screws respectively fixed to the vertebrae of the subject person is coupled as one device to perform the operation.

6 Claims, 18 Drawing Sheets

(56) References Cited

U.S. PATENT DOCUMENTS

| | | | | |
|---|---|---|---|---|
| 8,105,362 B2* | 1/2012 | Duarte | ............... | A61B 17/7089 606/264 |
| 9,402,659 B2* | 8/2016 | McBride | ............ | A61B 17/7077 |
| 2008/0051782 A1* | 2/2008 | Wu | ................... | A61B 17/7089 606/250 |
| 2009/0326586 A1* | 12/2009 | Duarte | ............... | A61B 17/7089 606/264 |
| 2015/0045834 A1* | 2/2015 | McBride | ............ | A61B 17/7077 606/264 |

FOREIGN PATENT DOCUMENTS

| | | |
|---|---|---|
| KR | 10-0811563 B1 | 3/2008 |
| KR | 10-0942226 B1 | 2/2010 |
| KR | 10-1067664 B1 | 9/2011 |
| KR | 10-1419807 B1 | 7/2014 |
| KR | 10-1434333 B1 | 8/2014 |

* cited by examiner (a)

(b)

ROD INSERTER FOR FIXING OF PEDICLE SCREW, SCREW HOLDER WITH JOINT FOR MINIMAL INVASIVE SURGERY, SCREW REDUCER FOR MINIMAL INVASIVE SURGERY AND APPARATUS FOR MINIMAL INVASIVE SURGERY USING THESE DEVICES

CROSS-REFERENCE TO RELATED APPLICATIONS

The present application claims priority under 35 U.S.C. 119 to Korean Patent Application Nos. 10-2015-0122344, 10-2015-0122345, and 10-2015-0122346, all of which were filed on Aug. 31, 2015, and the entire contents thereof are hereby incorporated by reference.

BACKGROUND

The present disclosure relates to an apparatus of a minimal invasive surgery, and more particularly, to a rod inserter for fixing a pedicle screw, which is capable of quickly and easily coupling one rod corresponding to lordosis of a person to be surgically operated (hereinafter, referred to as a subject person) to a plurality of screw heads respectively fixed to vertebrae of the subject person to perform a surgical operation, a screw holder with a joint for the minimal invasive surgery, a screw reducer for the minimal invasive surgery, and an apparatus for the minimal invasive surgery using these devices.

A disk between vertebrae functions as a joint and plays very important roles for minimizing an impact applied to the vertebrae while vertebral pulp changes in position and shape according to movement of the vertebrae.

When an operation for removing a seriously dented or damaged disk due to the aging, accidents, or the like is performed, measures for maintaining a space between vertebrae and preventing the vertebrae from being deformed or shaken have to be done.

For this, spine-disk patients may be operated according to following procedures.

That is, a disk corresponding to a damaged portion of the vertebra is removed so that the damaged portion of the vertebra is not pushed or pressed, and then, bone fragments are filled into a hollow artificial aid (cage) formed of a metal or plastic material, and the artificial aid is inserted into the portion of the vertebra from which the disk is removed.

Sequentially, a pedicle screw is inserted into each of portions of the vertebra, which correspond to upper and lower sides of the damaged disk, and then, a rod is connected to the pedicle screw to secure a distance between the vertebrae, thereby normally realizing osseointegration (hereinafter, referred to an operation 1).

When a disk between vertebrae is lightly damaged in spine-disk patients, an operation may be performed as follows. That is, the disk leaves it as it is, and a pedicle screw is inserted into and fixed to each of portions of the vertebra, which correspond to upper and lower sides of the damaged disk, and then, a rod is connected to the pedicle screw to secure a distance between the vertebrae, thereby preventing the damaged disk from being worsen (hereinafter, referred to as an operation 2).

However, since the operations 1 and 2 essentially require a process of cutting a skin corresponding to the damaged vertebra by a predetermined size so as to couple the rod to the pedicle screw after the pedicle screw is coupled to the vertebra, an invasive portion may be large to cause limitations in which recovery of the patient is delayed, and satisfaction after the operation is low due to the wound.

As the inventions from the foregoing points of view, there are Korean Patent Registration No. 10-0623441, titled "MINIMAL INVASIVE SPINE ROD INSERTER" (hereinafter, referred to as a 'prior art 1', Korean Patent Registration No. 10-0811563, titled "THE MINIMALLY INVASIVE INSTRUMENT OF SPINAL FIXATION DEVICE" (hereinafter, referred to as a 'prior art 2'), Korean Patent Registration No. 10-0942226, titled "ROD HOLDER AND MINIMALLY INVASIVE SYSTEM FOR SPINAL SURGICAL OPERATION USING THE SAME" (hereinafter, referred to as a 'prior art 3'), Korean Patent Registration No. 10-1067664, titled "MINIMALLY INVASIVE INSTRUMENT FOR SPINAL FIXATION" (hereinafter, referred to as a 'prior art 4'), and Korean Patent Registration No. 10-1419807, titled "WORKING TOWER FOR MINIMALLY INVASIVE SURGERY SYSTEM" (hereinafter, referred to as a 'prior art 5').

However, the prior arts 1 to 5 may be applied up to a 2-level operation, but may not be applied to 3-level or more operations.

Here, an n-level (where n is an integer equal to or greater than 1) denotes a state in which n+1 pedicle screws are respectively fixed to n+1 vertebrae.

Referring to FIG. 14, the prior arts 1 to 4, and particularly, the prior art 5 may not be applied to 3-level or more operations.

That is, in case of the prior art 5, a lower end of a screw holder 10 having both penetrated ends is detachably coupled to a head 41 of a pedicle screw 40 fixed to a vertebra (not shown).

Here, although not particularly shown, in case of a 1-level or 2-level operation, i.e., when the total 2 or 3 pedicle screws 40 are respectively fixed to 2 or 3 vertebrae, a rod insertion guide slot 11 that is cut upward by a predetermined length from both sides of an edge of the lower end of the screw holder 10 and a rod insertion groove 42 that is cut downward from both sides of an edge of an upper end of the head 41 communicate with each other.

Thus, the rod is inserted to pass through the rod insertion guide slot 11. Here, the prior art 5 in addition to the prior art 1 to 4 may be applied to only the 1-level or 2-level operation.

This is done because, in case of the prior arts 1 to 5, a fatal accident in which the screw holder 10 is separated from the head 41 due to the states of the pedicle screws 40 fixed to the vertebrae at various angles different from each other while an operator forcibly inserts one rod into the rod insertion guide slot 11 of each of five screw holders 10 in the state of a level exceeding a 3-level, i.e., the 4-level as illustrated in FIG. 14.

Particularly, in the state of the 3-level or more, the operation itself may be impossible in the prior arts 1 to 5. In addition, it is difficult to allow the rod that is elongated as the level number increases, for example, from the 1-level to the 2-level to pass to be inserted by using a single device.

Also, there are several technologies for reducing the spinal rod into the rear pedicle screw in the spine surgery fields.

The main technology may be designed so that the rod is individually reduced into each of the pedicle screws one level at a time by using a separate rod reducing mechanism such as rocker forks or ratchet-type mechanisms, which is connected to the head of the pedicle screw after the screw is inserted, and the rod is disposed.

In these reducing technologies, a large axial load may be applied to the pedicle screws.

The rod may match specific deformity and then be mounted inside the implanted pedicle screw. When the rod is mounted inside the implanted pedicle screw as described above, since the rod is bent to its original position, the deformity may be corrected.

However, in these technologies, a time is spent, and stress and deformation may be applied to the rod prior to the implantation.

The specific rod reducing technologies may use special reducing pedicle screws including upwardly extending integrated taps that are used to gradually reduce the rod over the whole length of the deformity. When the reducing is completed, the extending taps are separated from each other.

However, these technologies have a limitation in which the technologies are generally limited to only the reducing screw, and high costs are required for the implantation.

SUMMARY

Embodiments provide a rod inserter for fixing a pedicle screw through which an arc-shaped rods having lengths different from each other are coupled according to the number of screws that are respectively fixed to vertebrae of a subject person as one device to perform an operation and an apparatus for a minimal invasive surgery using the same.

Embodiments also provides a rod inserter for fixing a pedicle screw, which is capable of freely adjusting a radius defined by an arc-shaped rod that is capable of fixing all of a plurality of screws according to an increase of a level number depending on the number of screws and an apparatus for a minimal invasive surgery using the same.

Embodiments also provide a screw holder with a joint for a minimal invasive surgery, which is capable of quickly and easily fixing a head part of each of screws fixed to a relatively large number of vertebrae at a time by using one rod corresponding to a lordosis of a subject person and an apparatus for a minimal invasive surgery using the same.

Embodiments also provide a screw reducer for a minimal invasive surgery, which reduces a screw that is disposed at a height misaligned with a radius of a lordosis formed by lumbar of vertebrae of a subject person to help generation of the radius of the lordosis and an apparatus for a minimal invasive surgery using the same.

Embodiments provide a rod inserter for fixing a pedicle screw, the rod inserter including: a rotational support unit having a length corresponding to a radius of lordosis formed by lumbar of vertebrae of a subject person and of which a lower end is fixed; and a rotational insertion unit having a length corresponding to the radius and having one end rotatably coupled to an upper end of the rotational support unit and the other end to which an arc-shaped rod is detachably coupled, wherein each of the rotational support unit and the rotational insertion unit has a length that varies according to an increase or decrease of an n number in an n-level (where n is an integer equal to or greater than 1) that is in a state in which n+1 screws are respectively fixed to n+1 vertebrae.

The rotational support unit may include: a support cylinder of which a lower end is fixed; an accessible rod accommodated accessible through the support cylinder; a rotational bracket disposed on an upper end of the accessible rod and to which an upper end of the rotational insertion unit is rotatably coupled; and a first adjusting part disposed on each of the support cylinder and the accessible rod to maintain a state in which the accessible rod is withdrawn or accommodated through the support cylinder.

The first adjusting part may include: a first operation housing disposed on an upper end of the support cylinder to define an operation space therein; a first adjusting body built in the first operation housing, having one end exposed from an outer surface of the first operation housing, through which the accessible rod passes, and reciprocated in a direction perpendicular to the accessible direction of the accessible rod; a first biasing means disposed between the other end of the first adjusting body and an inner surface of the first operation housing to generate supporting force in a direction in which the first adjusting body protrudes to the outside of the first operation housing; a first operation control unit disposed on each of the support cylinder, an outer circumferential surface of the accessible rod, and the first adjusting body, the first operation control unit being engaged with the accessible rod or released from the engagement according to the reciprocation of the first adjusting body to allow or restrict the withdrawal or accommodation of the accessible rod with respect to the support cylinder.

The first adjusting body may include: a first reciprocation piece through which the accessible rod passes and reciprocated within the first operation housing; a first pushing piece extending from one end of the first reciprocation piece and exposed from a first access slot passing through an outer surface of the first operation housing, wherein the first biasing means is disposed between the other end of the first reciprocation piece and an inner surface of the first operation housing, and a portion of the first operation control means is disposed on the first reciprocation piece.

The rotational insertion unit may include: a rotational bar rotatably coupled to the upper end of the rotational support unit; an accessible cylinder coupled to an end of the rotational bar to accommodate the rotational bar so that the accessible cylinder is accessible through the rotational bar, wherein the accessible cylinder together with the rotational bar varies in total length; a connection bracket extending from an end of the accessible cylinder to form a portion of the arc shape; an insertion guide body detachably coupled to the connection bracket to form the rest portion of the arc shape; and a second adjusting part disposed on each of the rotational bar and the accessible cylinder to maintain a state in which the accessible cylinder is withdrawn or accommodated through the rotational bar, wherein the arc-shaped rod is detachably coupled to an end of the insertion guide body, and the connection bracket, the insertion guide body, and the arc-shaped rod form an arc corresponding to the radius of the lordosis.

The second adjusting part may include: a second operation housing disposed on an upper end of the accessible cylinder to define an operation space therein; a second adjusting body built in the second operation housing, having one end exposed from an outer surface of the second operation housing, through which the rotational bar passes, and reciprocated in a direction perpendicular to the accessible direction of the rotational bar; a second biasing means disposed between the other end of the second adjusting body and an inner surface of the second operation housing to generate supporting force in a direction in which the second adjusting body protrudes to the outside of the second operation housing; a second operation control unit disposed on each of the accessible cylinder, an outer circumferential surface of the rotational bar, and the second adjusting body, the second operation control unit being engaged with the rotational bar or released from the engagement according to the reciprocation of the second adjusting body to allow or restrict the withdrawal or accommodation of the rotational bar with respect to the accessible cylinder.

The second adjusting body may include: a second reciprocation piece through which the rotation bar passes and reciprocated within the second operation housing; a second pushing piece extending from one end of the second reciprocation piece and exposed from a second access slot passing through an outer surface of the second operation housing, wherein the second biasing means is disposed between the other end of the second reciprocation piece and an inner surface of the second operation housing, and a portion of the second operation control means is disposed on the second reciprocation piece.

In one embodiment, an apparatus for a minimal invasive surgery using a rod inserter for fixing a pedicle screw includes: a holder unit including a holder body having both penetrated ends and a detachable part rotatably coupled to an end of the holder body and coupled to a head part of the screw fixed to a vertebra; an alignment unit that clamps upper portions of the holder bodies respectively coupled to the plurality of head parts at the same time to align the upper portions of the holder units in a straight line; and an insertion unit including a rotation support unit having a length corresponding to a radius of lordosis formed by lumbar of a vertebra of a subject person and of which a lower end is fixed and a rotational insertion unit having a length corresponding to the radius and having one end rotatably coupled to an upper end of the rotational support unit and the other end to which an arc-shaped rod is detachably coupled, wherein each of the rotational support unit and the rotational insertion unit has a length that varies according to an increase or decrease of an n number in an n-level (where n is an integer equal to or greater than 1) that is in a state in which n+1 screws are respectively fixed to n+1 vertebrae.

The detachable part may be rotatable with respect to the holder body so that the head part of the screw fixed to each of a plurality of vertebrae including the vertebra and vertebrae adjacent to the vertebra corresponds to tilted angles different from each other, which are angled with respect to the plurality of vertebrae, and the detachable part may further include a rod insertion guide groove that guides coupling of the arc-shaped rod coupled to pass through the head part fixed to each of plurality of vertebrae.

The alignment unit may include: a pair of grip parts rotatable with respect to a clamping shaft; and a clamping bar extending from each of the pair of grip parts, spread with respect to each other while moving in a direction in which the pair of grip parts approach each other, moving in a direction in which the pair of grip parts contact each other when force applied to the pair of grip parts is removed, and clamping the upper portions of the plurality of holder bodies at the same time, wherein the insertion unit is coupled to an outer surface of one clamping bar of the pair of clamping bars.

In another embodiment, a screw holder with a joint for a minimal invasive surgery includes: a holder body having both penetrated ends; and a detachable part rotatably coupled to an end of the holder body and coupled to a head part of a screw fixed to a vertebra.

The holder body may include: a support part having both penetrated ends; a stepped part having a diameter greater than the support part and disposed to be stepped on an upper portion of the support part; a screw thread disposed along an outer circumferential surface of the stepped part; and alignment contact surfaces disposed on both sides of the outer circumferential surface of the stepped part to face each other and each of which is stepped with a predetermined length and width downward from an edge of an upper end of the stepped part, wherein the detachable part attached to or detached from the head part is rotatably coupled to both sides of an outer circumferential surface of a lower end of the support part.

The detachable part may be rotatable with respect to the holder body so that the head part of the screw fixed to each of a plurality of vertebrae including the vertebra and vertebrae adjacent to the vertebra corresponds to tilted angles different from each other, which are angled with respect to the plurality of vertebrae, and the detachable part further include a rod insertion guide groove that guides coupling of the arc-shaped rod coupled to pass through the head part fixed to each of plurality of vertebrae.

The plurality of vertebrae may include two or more vertebrae.

In further another embodiment, an apparatus for a minimal invasive surgery using a screw holder with a joint for the minimal invasive surgery includes: a holder unit including a holder body having both penetrated ends and a detachable part rotatably coupled to an end of the holder body and coupled to a head part of the screw fixed to a vertebra; an alignment unit that clamps upper portions of the holder bodies respectively coupled to the plurality of head parts at the same time to align the upper portions of the holder units in a straight line; and an insertion unit disposed on one side of the alignment unit to insert a rod having an arc shape corresponding to a radius of lordosis formed by lumbar of a vertebra of a subject person and thereby to pass through the detachable parts.

The detachable part may be rotatable with respect to the holder body so that the head part of the screw fixed to each of a plurality of vertebrae including the vertebra and vertebrae adjacent to the vertebra corresponds to tilted angles different from each other, which are angled with respect to the plurality of vertebrae, and the detachable part may further include a rod insertion guide groove that guides coupling of the arc-shaped rod coupled to pass through the head part fixed to each of plurality of vertebrae.

The plurality of vertebrae may include two or more vertebrae.

The alignment unit may include: a pair of grip parts rotatable with respect to a clamping shaft; and a clamping bar extending from each of the pair of grip parts, spread with respect to each other while moving in a direction in which the pair of grip parts approach each other, moving in a direction in which the pair of grip parts contact each other when force applied to the pair of grip parts is removed, and clamping the upper portions of the plurality of holder bodies at the same time, wherein the insertion unit is coupled to an outer surface of one clamping bar of the pair of clamping bars.

The insertion unit may include: a rotation support part of which a lower end is mounted on one side of the alignment unit; and a rotation insertion part having a length corresponding to the radius of the lordosis, having an end to which the arc-shaped rod is detachably coupled, and rotatably coupled to an upper end of the rotation support part, wherein the arc-shaped rod passes to be inserted into each of the detachable parts rotatably coupled to the holder body by rotation of the rotation insertion part.

The rotational insertion unit may include: a rotational bar rotatably coupled to the upper end of the rotational support unit; an accessible cylinder coupled to an end of the rotational bar to accommodate the rotational bar so that the accessible cylinder is accessible through the rotational bar, wherein the accessible cylinder together with the rotational bar varies in total length; a connection bracket extending from an end of the accessible cylinder to form a portion of the arc shape; and an insertion guide body detachably coupled to the connection bracket to form the rest portion of the arc shape, wherein the arc-shaped rod is detachably coupled to an end of the insertion guide body, and the connection bracket, the insertion guide body, and the arc-shaped rod form an arc corresponding to the radius of the lordosis.

In still further another embodiment, a screw reducer for a minimal invasive surgery, the screw reducer includes a corrector reducing a screw disposed at a height misaligned with a radius of lordosis formed by lumbar among a plurality of screws respectively fixed to a plurality of vertebrae that form lumbar of vertebrae of a subject person to form an arc shape corresponding to the radius of the lordosis.

The screw reducer may further include: a head part coupled to an upper end of the screw; a holder unit including a detachable part having both penetrated ends, which is coupled to the head part, a holder body coupled to an upper end of the detachable part so that the detachable part is rotatable, and an alignment nut coupled to a screw thread disposed on an upper portion of the holder body; and an alignment unit that clamps upper portions of the holder bodies respectively coupled to the plurality of head parts at the same time to align the upper portions of the holder units in a straight line, wherein the screw disposed at the misaligned height is reduced by the corrector coupled to the alignment nut in a state in which the plurality of holder units are disposed in a straight line by the alignment unit.

The corrector may include: a correction body having an opened bottom surface to form a reducing space; a hook protrusion protruding upward from a lower end of an inner surface of the correction body and having a shape corresponding to an outer surface of the alignment nut coupled to a screw thread disposed on an upper portion of the holder unit that is attachable to or detachable from the head part coupled to an upper end of the screw, wherein the screw disposed at the misaligned height is reduced as the correction body coupled to the alignment nut is rotated in place in a state where the plurality of holder units are arranged in a straight line.

A height of the hook protrusion, which is defined from a bottom surface of the correction body, may be equal to or greater than that of the alignment nut.

A distance from a bottom surface of the correction body to a top surface of the reducing space may be greater than that by which an upper portion of the holder unit coupled to the upper end of the screw disposed at the misaligned height protrudes from the alignment nut.

The corrector may further include: a support shaft extending from a top surface of the correction body; and a rotational handle disposed on an upper end of the support shaft, wherein the support shaft and the rotational handle are integrally rotated with the correction body.

In much further another embodiment, an apparatus for a minimal invasive surgery using a screw reducer for the minimal invasive surgery includes: a corrector reducing a screw disposed at a height misaligned with a radius of lordosis formed by lumbar among a plurality of screws respectively fixed to a plurality of vertebrae that form lumbar of vertebrae of a subject person to form an arc shape corresponding to the radius of the lordosis; a holder unit including a detachable part having both penetrated ends, which is coupled to a head part coupled to an upper end of the screw, a holder body coupled to an upper end of the detachable part so that the detachable part is rotatable, and an alignment nut coupled to a screw thread disposed on an upper portion of the holder body; and an alignment unit that clamps upper portions of the holder bodies respectively coupled to the plurality of head parts at the same time to align the upper portions of the holder units in a straight line, wherein the screw disposed at the misaligned height is reduced by the corrector coupled to the alignment nut in a state in which the plurality of holder units are disposed in a straight line by the alignment unit.

The corrector may include: a correction body having an opened bottom surface to form a reducing space; a hook protrusion protruding upward from a lower end of an inner surface of the correction body and having a shape corresponding to an outer surface of the alignment nut coupled to a screw thread disposed on an upper portion of the holder unit that is attachable to or detachable from the head part coupled to an upper end of the screw, wherein the screw disposed at the misaligned height is reduced as the correction body coupled to the alignment nut is rotated in place in a state where the plurality of holder units are arranged in a straight line.

The alignment unit may include: a pair of grip parts rotatable with respect to a clamping shaft; and a clamping bar extending from each of the pair of grip parts, spread with respect to each other while moving in a direction in which the pair of grip parts approach each other, moving in a direction in which the pair of grip parts contact each other when force applied to the pair of grip parts is removed, and clamping the upper portions of the plurality of holder bodies at the same time, wherein a bottom surface of the corrector faces an edge of an upper portion of the clamping bar, and as the corrector coupled to the alignment nut is rotated in place, the screw disposed at the misaligned height, the head part, the detachable part, and the holder body are integrally reduced.

The alignment unit may further include an insertion unit coupled to an outer surface of one clamping bar of the pair of clamping bars to insert a rod having an arc shape corresponding to a radius of lordosis formed by lumbar of a vertebra of a subject person and thereby to pass through the detachable parts.

The details of one or more embodiments are set forth in the accompanying drawings and the description below. Other features will be apparent from the description and drawings, and from the claims.

BRIEF DESCRIPTION OF THE DRAWINGS

FIG. 13 is a view illustrating a state in which the clamping bar contacts the alignment contact surface to reduce the alignment nut along a screw thread of the holder unit, FIG. 14 is a view illustrating a state in which the alignment nuts are reduced to be aligned with an upper portion of an edge of the clamping bar, and FIG. 15 is a perspective view illustrating a preparation state for coupling an insertion unit to the alignment unit to insert the arc-shaped rod.

DETAILED DESCRIPTION OF THE EMBODIMENTS

Figure 1:
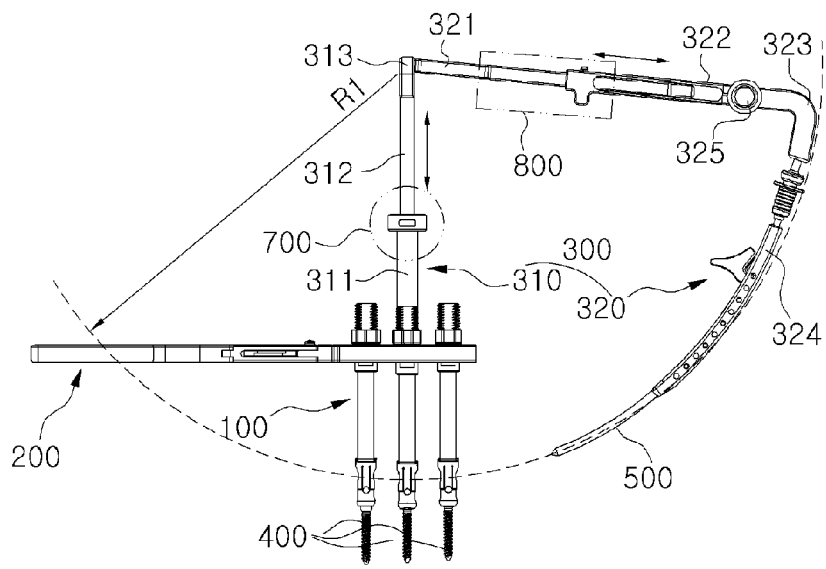
FIG. 1 is a view illustrating a state for inserting an arc-shaped rod by using a rod inserter for fixing a pedicle screw according to an embodiment, i.e., FIG. 1 panel (a) is a view illustrating a state for inserting the arc-shaped rod in a 2-level state, and FIG. 1 panel (b) is a side-conceptual view illustrating a state in which the arc-shaped rod is inserted in a 4-level state.
Figure 1:
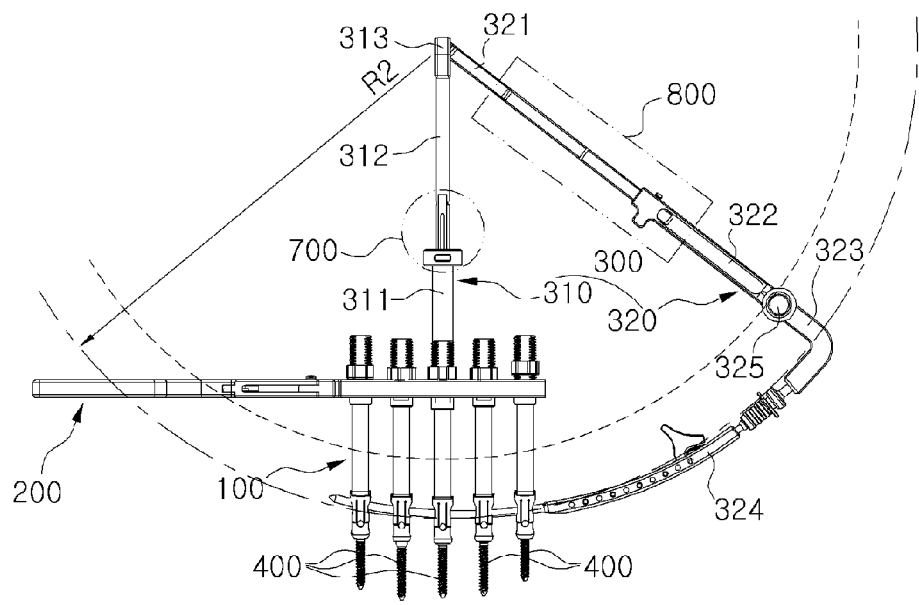

Advantages and features of the present disclosure, and implementation methods thereof will be clarified through following embodiments described with reference to the accompanying drawings.

The present disclosure may, however, be embodied in different forms and should not be construed as limited to the embodiments set forth herein.

In this specification, these embodiments are provided so that this disclosure will be thorough and complete, and will fully convey the scope of the present disclosure to those skilled in the art.

Also, the present disclosure is only defined by scopes of claims.

Accordingly, in some embodiments, well-known components, well-known device operations, and well-known techniques will not be described in detail to avoid ambiguous interpretation of the present disclosure.

Also, like reference numerals refer to like elements throughout. In the following description, the technical terms are used only for explaining a specific exemplary embodiment while not limiting the present disclosure.

The terms of a singular form may include plural forms unless referred to the contrary. The meaning of "include," "comprise," "including," or "comprising," specifies a component and an operation but does not exclude other components and operations.

Unless terms used in the present disclosure are defined differently, all terms (including technical and scientific terms) used herein have the same meaning as generally understood by those skilled in the art. Terms as defined in a commonly used dictionary should be construed as having the same meaning as in an associated technical context.

Also, unless defined apparently in the description, the terms are not ideally or excessively construed as having formal meaning.

Preferred embodiments of the present invention will be described below in more detail with reference to the accompanying drawings.

For reference, FIG. 1 is a view illustrating a state for inserting an arc-shaped rod 500 by using a rod inserter for fixing a pedicle screw according to an embodiment, i.e., FIG. 1 panel (a) is a view illustrating a state for inserting the arc-shaped rod 500 in a 2-level state, and FIG. 1 panel (b) is a side-conceptual view illustrating a state in which the arc-shaped rod 500 is inserted in a 4-level state.

Figure 2:
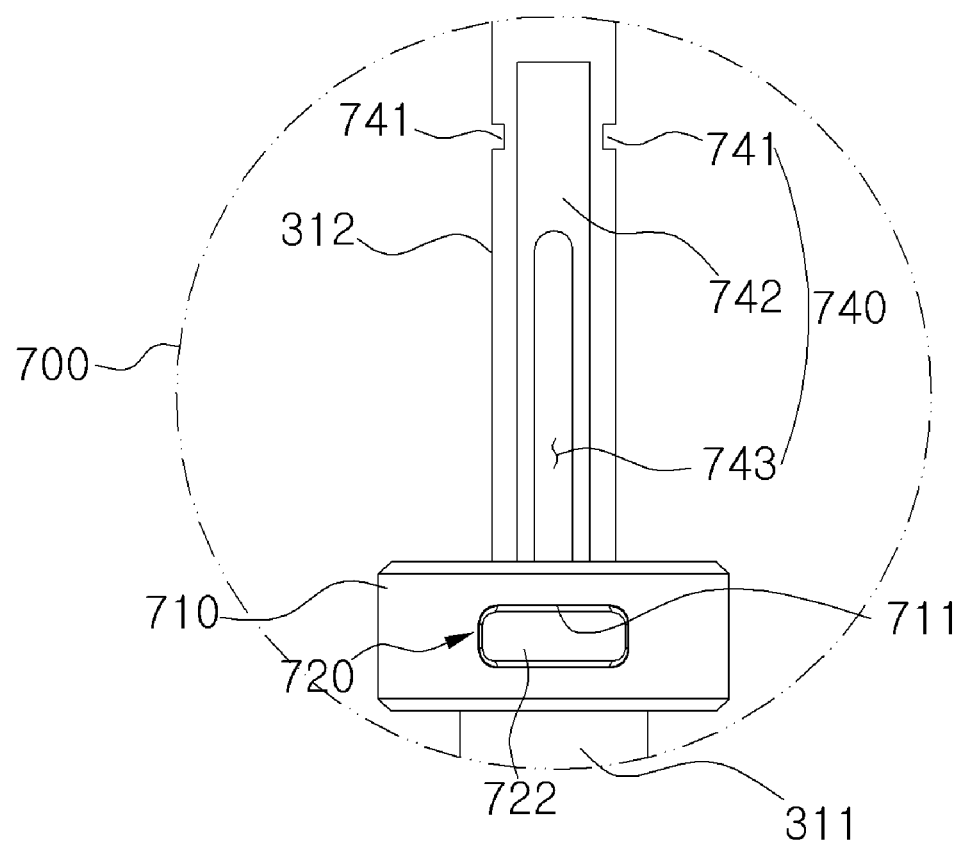
FIG. 2 is an enlarged side-conceptual view illustrating an outer appearance of a first adjusting part disposed on a rotational support unit that is a main part of the rod inserter for fixing the pedicle screw in FIG. 1 panel (b) according to an embodiment.

Also, FIG. 2 is an enlarged side-conceptual view illustrating an outer appearance of a first adjusting part 700 disposed on a rotational support unit 310 that is a main part of the rod inserter for fixing the pedicle screw in FIG. 1 panel (b) according to an embodiment.

Figure 3:
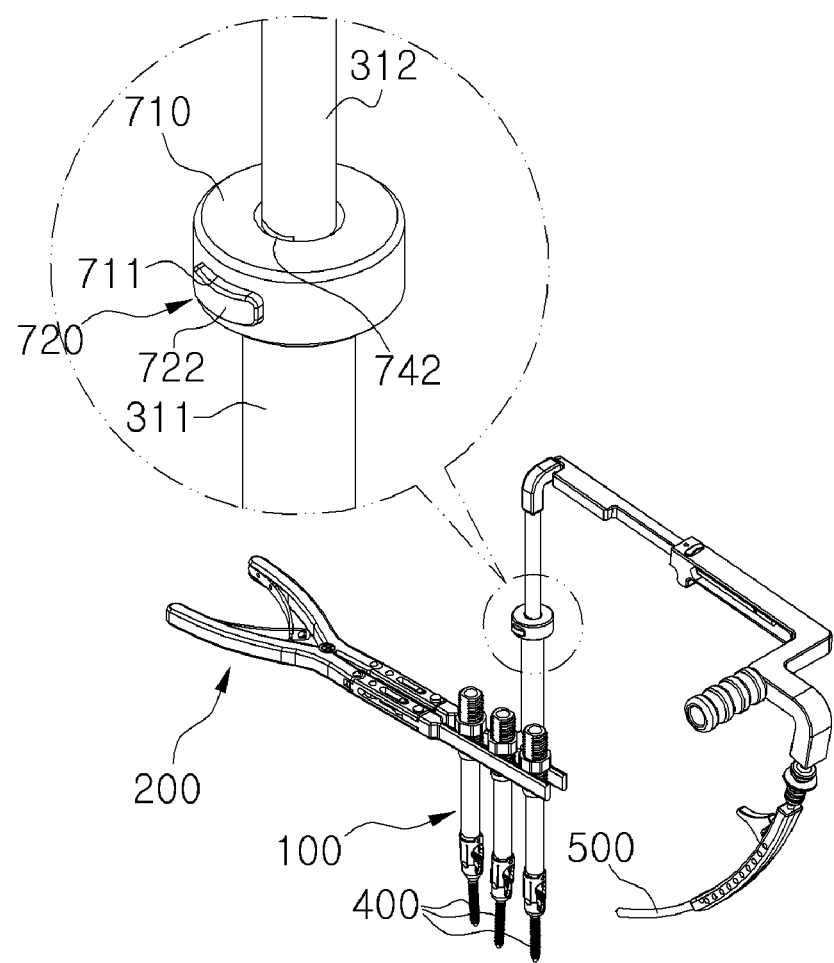
FIG. 3 is an enlarged perspective view illustrating the outer appearance of the first adjusting part disposed on the rotational support unit that is a main part of the rod inserter for fixing the pedicle screw on the basis of surrounding portions of a support cylinder and an accessible rod according to an embodiment.

Also, FIG. 3 is an enlarged perspective view illustrating the outer appearance of the first adjusting part 700 disposed on the rotational support unit 310 that is a main part of the rod inserter for fixing the pedicle screw on the basis of surrounding portions of a support cylinder 311 and an accessible rod 312 according to an embodiment.

Figure 4:
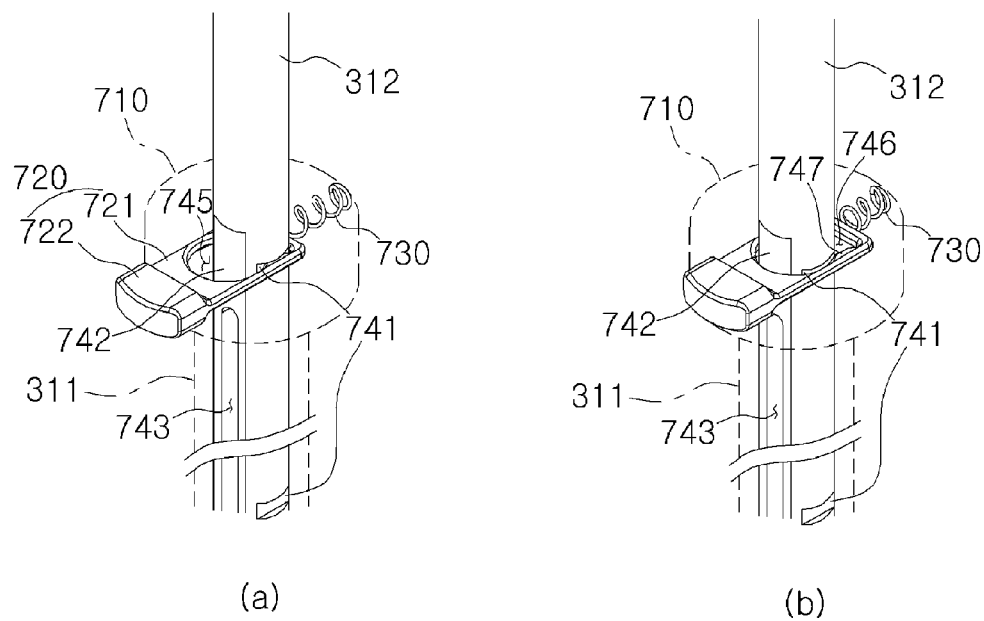
FIG. 4 is a view illustrating an operation state of the first adjusting part disposed on the rotational support unit that is a main part of the rod inserter for fixing the pedicle screw according to an embodiment, i.e., FIG. 4 panel (a) is a view illustrating a state in which entrance of the accessible rod into the support cylinder is restricted before force is applied to a first biasing means, and FIG. 4 panel (b) is a perspective view illustrating a state in which the entrance of the accessible rod into the support cylinder is allowed after the force is applied to the first biasing means.

Also, FIG. 4 is a view illustrating an operation state of the first adjusting part 700 disposed on the rotational support unit 310 that is a main part of the rod inserter for fixing the pedicle screw according to an embodiment, i.e., FIG. 4 panel (a) is a view illustrating a state in which entrance of the accessible rod 312 into the support cylinder 311 is restricted before force is applied to a first biasing means 730, and FIG. 4 panel (b) is a perspective view illustrating a state in which the entrance of the accessible rod 312 into the support cylinder 311 is allowed after the force is applied to the first biasing means 730.

Figure 5:
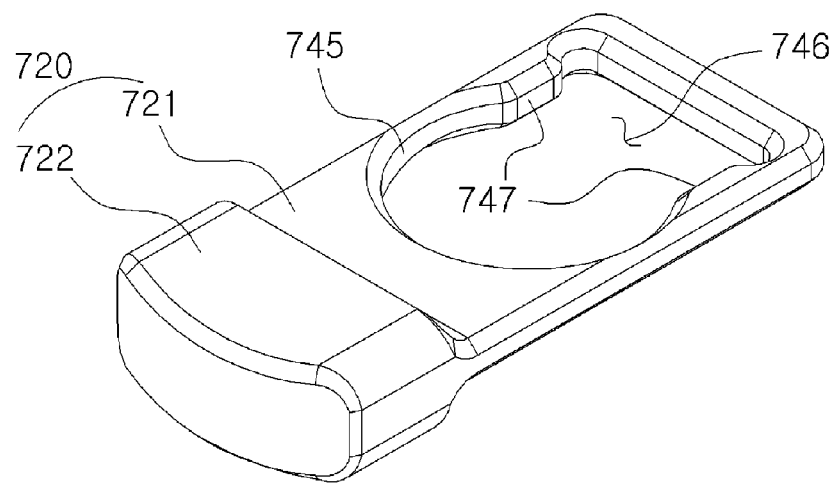
FIG. 5 is a perspective view illustrating portions of a first adjusting body and a first operation control means of the first adjusting part that is a main part of the rod inserter for fixing the pedicle screw according to an embodiment.

Also, FIG. 5 is a perspective view illustrating portions of a first adjusting body 720 and a first operation control means 740 of the first adjusting part that is a main part of the rod inserter for fixing the pedicle screw according to an embodiment.

Figure 6:
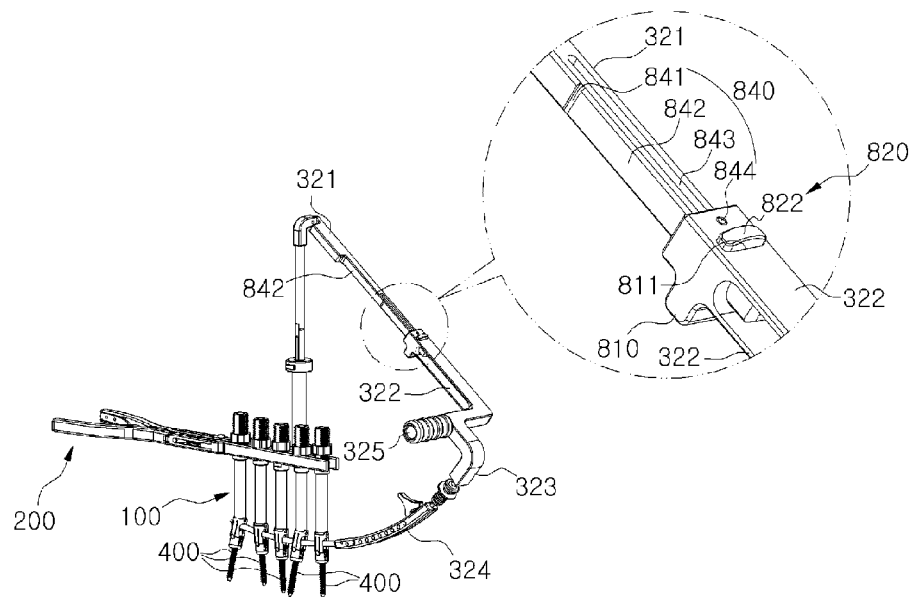
FIG. 6 is an enlarged perspective view illustrating an outer appearance of a second adjusting part disposed on a rotational insertion unit that is a main part of the rod inserter for fixing the pedicle screw on the basis of surrounding portions of a rotational bar and an accessible cylinder according to an embodiment.

Also, FIG. 6 is an enlarged perspective view illustrating an outer appearance of a second adjusting part 800 disposed on a rotational insertion unit 320 that is a main part of the rod inserter for fixing the pedicle screw on the basis of surrounding portions of a rotational bar 321 and an accessible cylinder 322 according to an embodiment.

Figure 7:
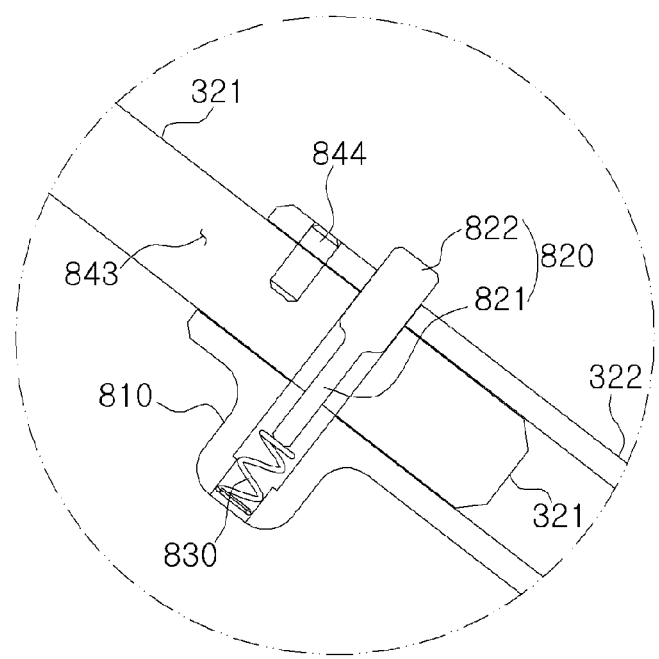
FIG. 7 is a cross-sectional conceptual view illustrating an inner structure of the second adjusting part disposed on the rotational insertion unit that is a main part of the rod inserter for fixing the pedicle screw according to an embodiment.

Also, FIG. 7 is a cross-sectional conceptual view illustrating an inner structure of the second adjusting part 800 disposed on the rotational insertion unit 320 that is a main part of the rod inserter for fixing the pedicle screw according to an embodiment.

Figure 8:
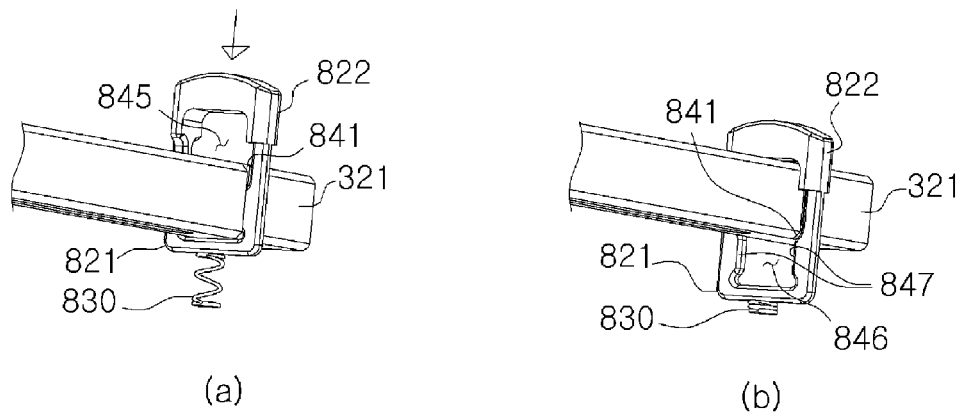
FIG. 8 is a view illustrating an operation state of the second adjusting part disposed on the rotational insertion unit that is a main part of the rod inserter for fixing the pedicle screw according to an embodiment, i.e., FIG. 8 panel (a) is a view illustrating a state in which the entrance of the accessible cylinder into the rotational bar is restricted before force is applied to a second biasing means, and FIG. 8 panel (b) is a perspective view illustrating a state in which the entrance of the accessible cylinder into the rotational bar is allowed after the force is applied to the second biasing means.

Also, FIG. 8 is a view illustrating an operation state of the second adjusting part 800 disposed on the rotational insertion unit 320 that is a main part of the rod inserter for fixing the pedicle screw according to an embodiment, i.e., FIG. 8 panel (a) is a view illustrating a state in which the entrance of the accessible cylinder 322 into the rotational bar 321 is restricted before force is applied to a second biasing means 830, and FIG. 8 panel (b) is a perspective view illustrating a state in which the entrance of the accessible cylinder 322 into the rotational bar 321 is allowed after the force is applied to the second biasing means 830.

Figure 9:
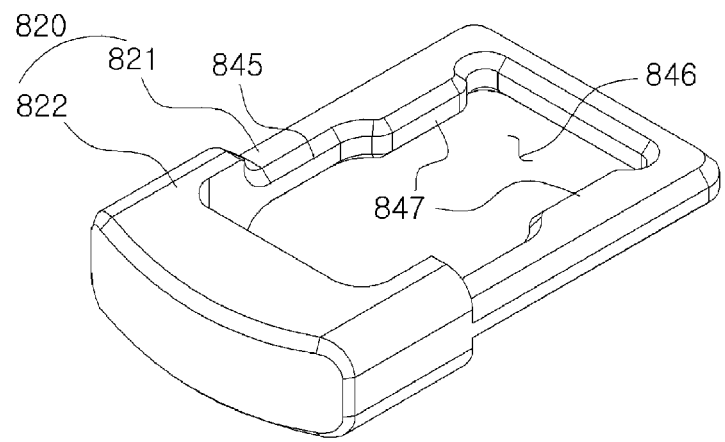
FIG. 9 is a perspective view illustrating portions of a second adjusting body and a second operation control means of the second adjusting part that is a main part of the rod inserter for fixing the pedicle screw according to an embodiment.

Also, FIG. 9 is a perspective view illustrating portions of a second adjusting body 820 and a second operation control means 840 of the second adjusting part 800 that is a main part of the rod inserter for fixing the pedicle screw according to an embodiment.

Figure 10:
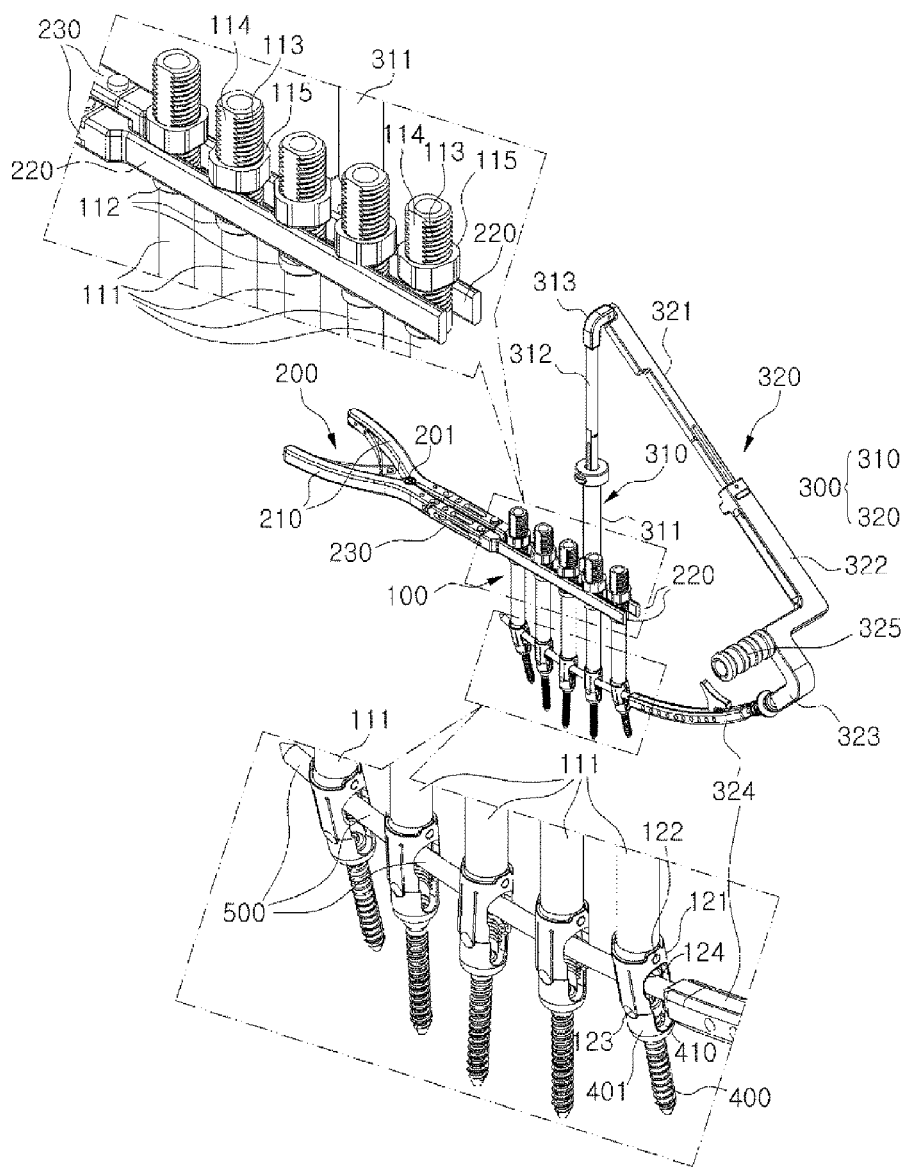
FIG. 10 is a perspective view illustrating an overall structure of an apparatus for a minimal invasive surgery using the rod inserter for fixing the pedicle screw according to an embodiment.

Also, FIG. 10 is a perspective view illustrating an overall structure of an apparatus for a minimal invasive surgery using the rod inserter for fixing the pedicle screw according to an embodiment.

Figure 11:
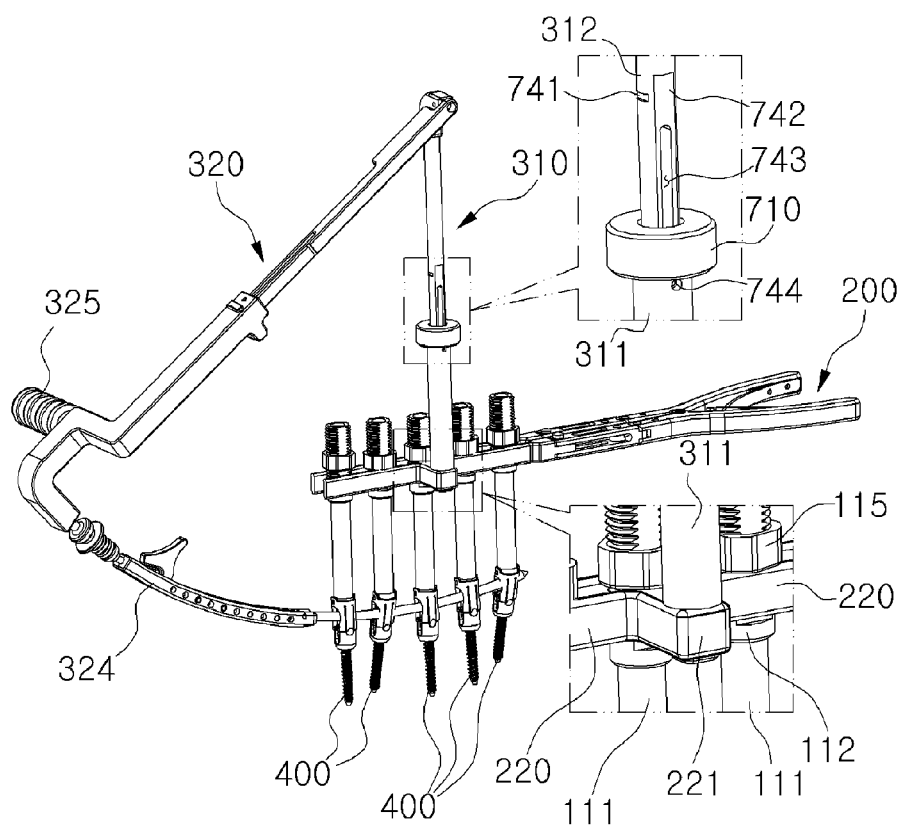
FIG. 11 is a perspective view illustrating the apparatus for the minimal invasive surgery using the rod inserter for fixing the pedicle screw when viewed in a direction opposite to that of FIG. 10 according to an embodiment.

Also, FIG. 11 is a perspective view illustrating the apparatus for the minimal invasive surgery using the rod inserter for fixing the pedicle screw when viewed in a direction opposite to that of FIG. 10 according to an embodiment.

Figure 12:
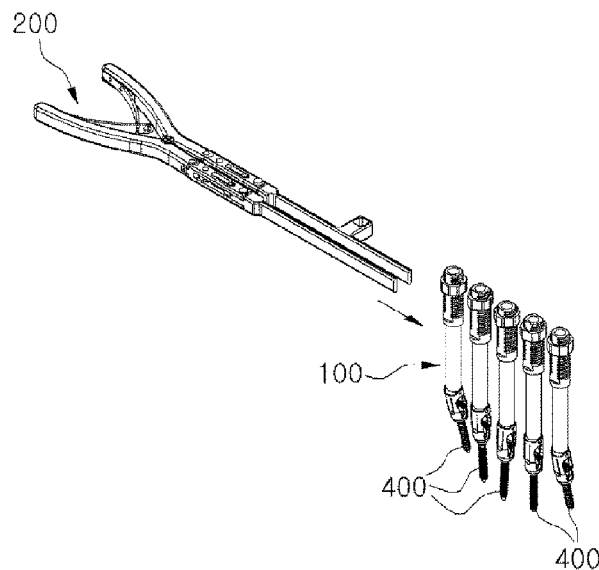
FIGS. 12 to 15 are views successively illustrating operation processes using the apparatus for the minimal invasive surgery using he rod inserter for fixing the pedicle screw according to an embodiment, i.e., FIG. 12 a view illustrating a state in which a clamping bar of an alignment unit approaches an alignment contact surface of a holder unit in a state in which the screw is fixed to each of a plurality of vertebrae.
Figure 13:
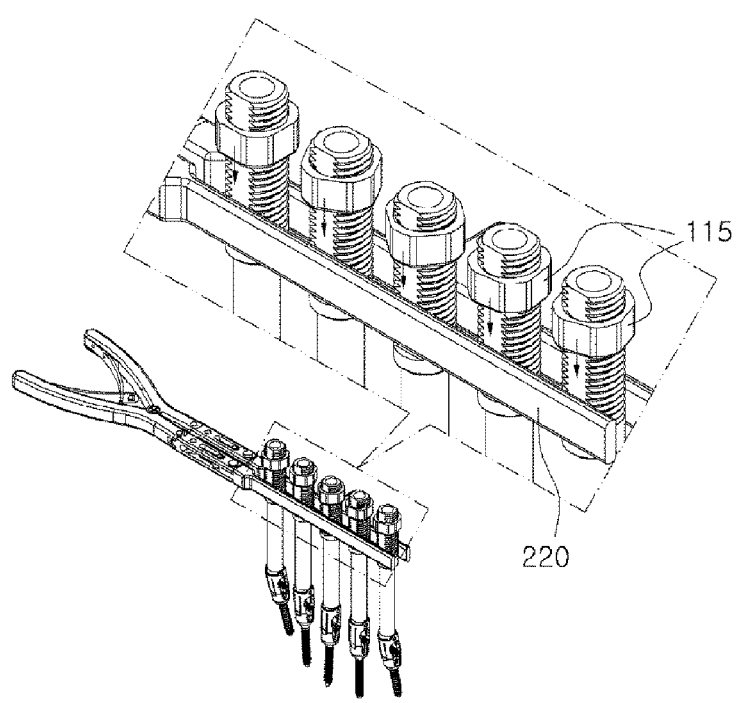
Figure 14:
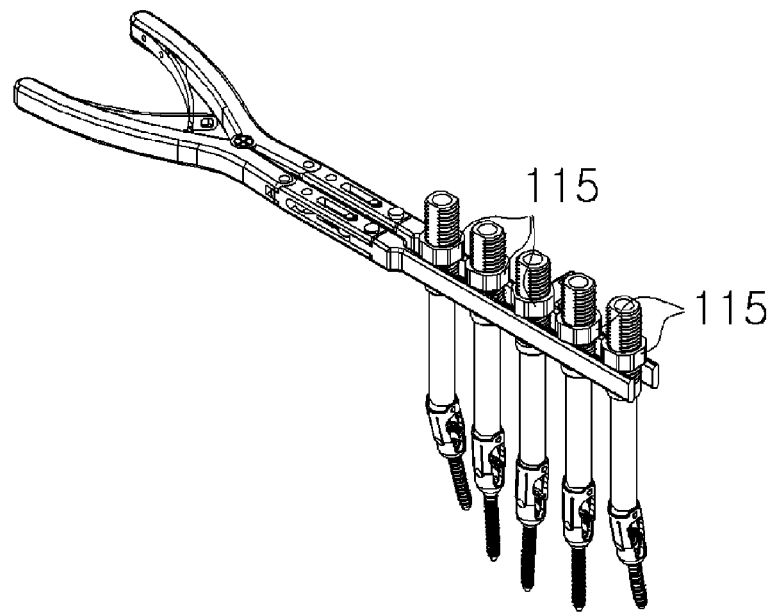
Figure 15:
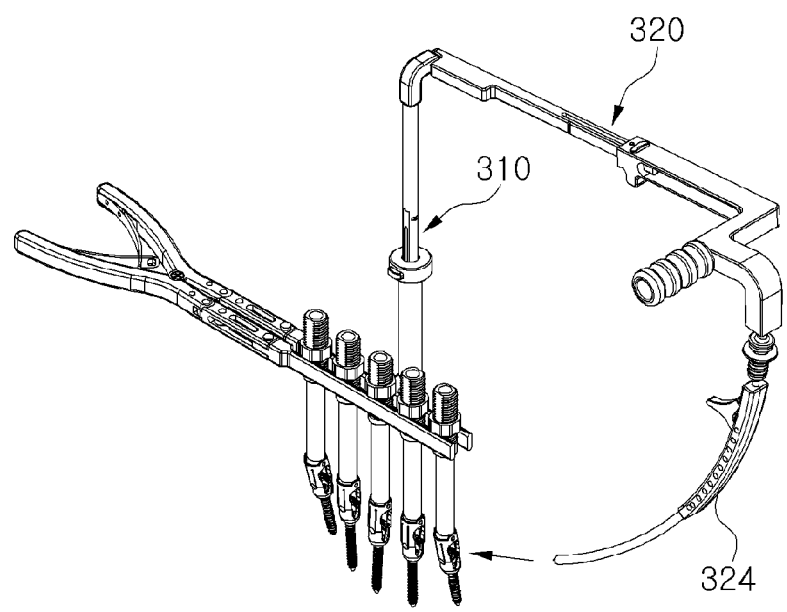

Also, FIGS. 12 to 15 are views successively illustrating operation processes using the apparatus for the minimal invasive surgery using he rod inserter for fixing the pedicle screw according to an embodiment, i.e., FIG. 12 a view illustrating a state in which a clamping bar 220 of an alignment unit 200 approaches an alignment contact surface 114 of a holder unit 100 in a state in which the screw is fixed to each of a plurality of vertebrae, FIG. 13 is a view illustrating a state in which the clamping bar 220 contacts the alignment contact surface 114 to reduce the alignment nut 115 along a screw thread of the holder unit 100, FIG. 14 is a view illustrating a state in which the alignment nuts 115 are reduced to be aligned with an upper portion of an edge of the clamping bar 220, and FIG. 15 is a perspective view illustrating a preparation state for coupling an insertion unit 300 to the alignment unit 200 to insert the arc-shaped rod 500.

Figure 16:
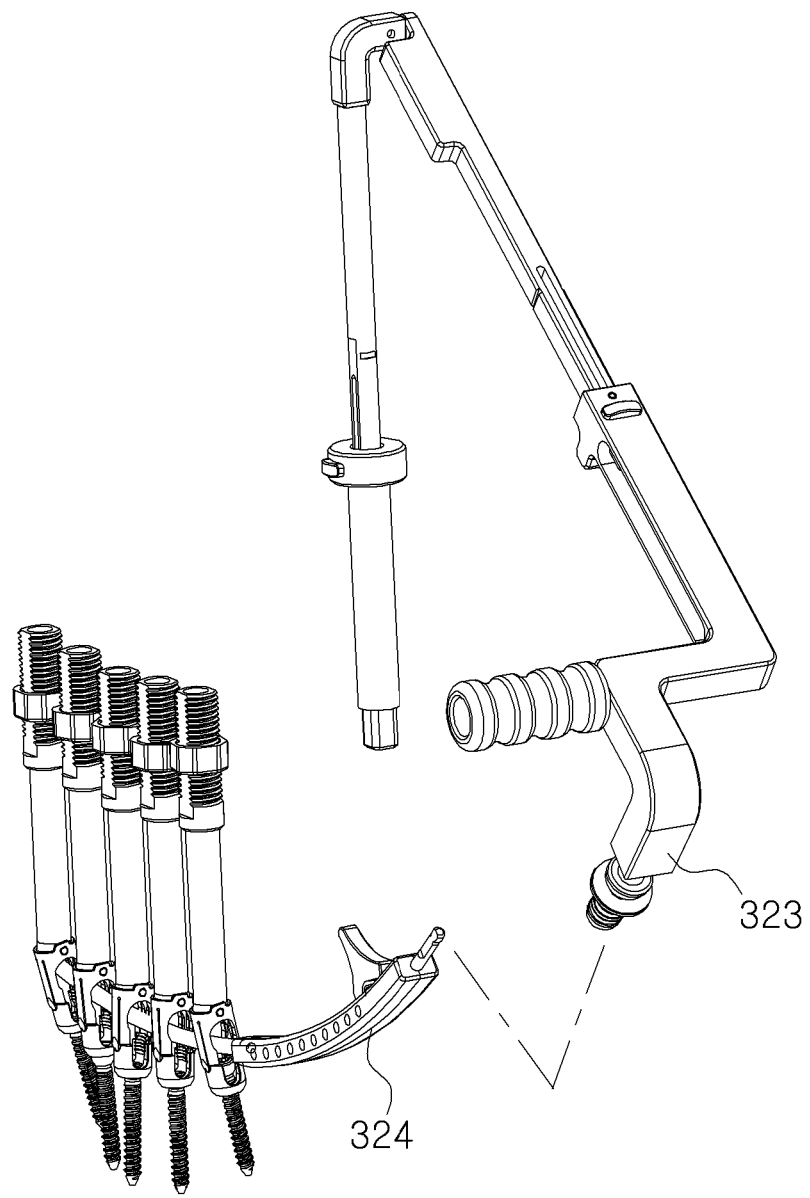
FIG. 16 is a partial exploded perspective view illustrating a state in which an insertion guide body of the insertion unit of an apparatus for a minimal invasive surgery using a rod inserter for fixing a pedicle screw is separated from a connection bracket according to an embodiment.

Also, FIG. 16 is a partial exploded perspective view illustrating a state in which an insertion guide body 324 of the insertion unit 300 of an apparatus for a minimal invasive surgery using a rod inserter for fixing a pedicle screw is separated from a connection bracket 323 according to an embodiment.

Figure 17:
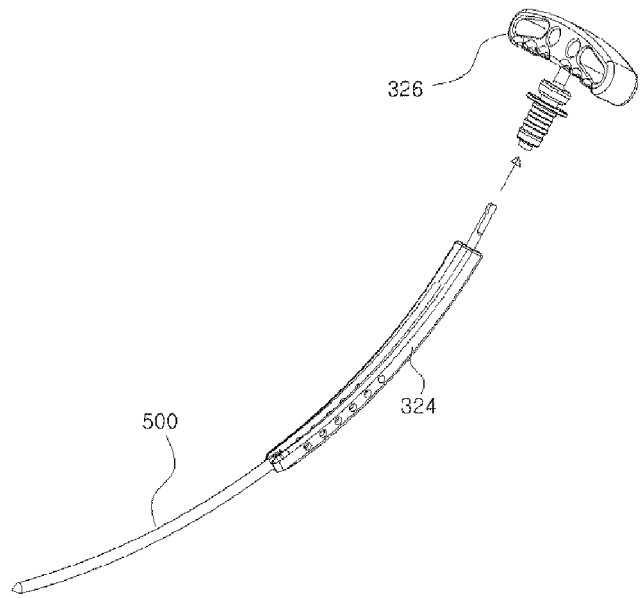
FIG. 17 is an exploded perspective view illustrating a state for coupling a manual insertion handle to the insertion guide body of the insertion unit of the apparatus for the minimal invasive surgery using the rod inserter for fixing the pedicle screw according to another embodiment.

Also, FIG. 17 is an exploded perspective view illustrating a state for coupling a manual insertion handle 326 to the insertion guide body 324 of the insertion unit 300 of the apparatus for the minimal invasive surgery using the rod inserter for fixing the pedicle screw according to another embodiment.

Figure 18:
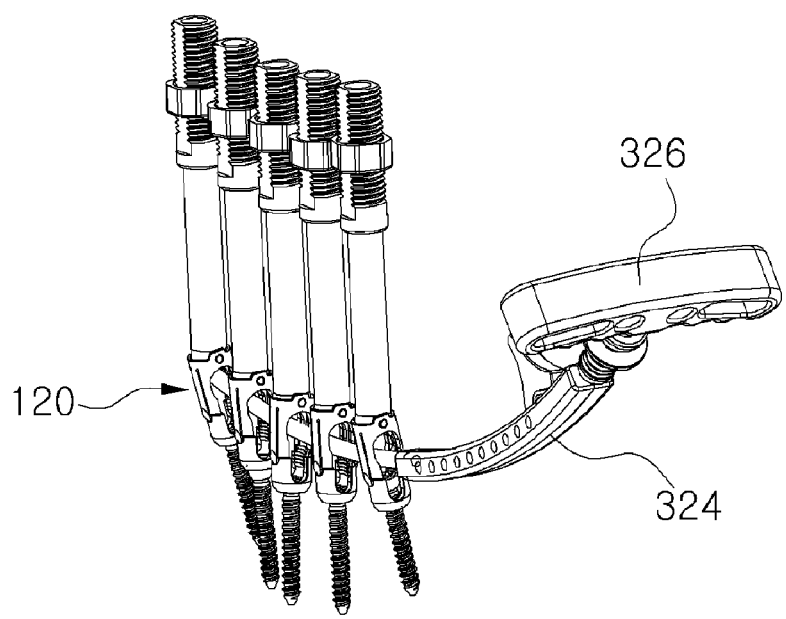
FIG. 18 is a perspective view illustrating a state in which an arc-shaped rod is coupled to the insertion guide body, to which the manual insertion handle to the insertion guide body of the insertion unit of the apparatus for the minimal invasive surgery using the rod inserter for fixing the pedicle screw is coupled, and inserted to pass through a detachable part having a 3-level or more according to another embodiment.

Also, FIG. 18 is a perspective view illustrating a state in which an arc-shaped rod 500 is coupled to the insertion guide body 324, to which the manual insertion handle 326 to the insertion guide body of the insertion unit of the apparatus for the minimal invasive surgery using the rod inserter for fixing the pedicle screw is coupled, and inserted to pass through a detachable part 120 having a 3-level or more according to another embodiment.

Figure 20:
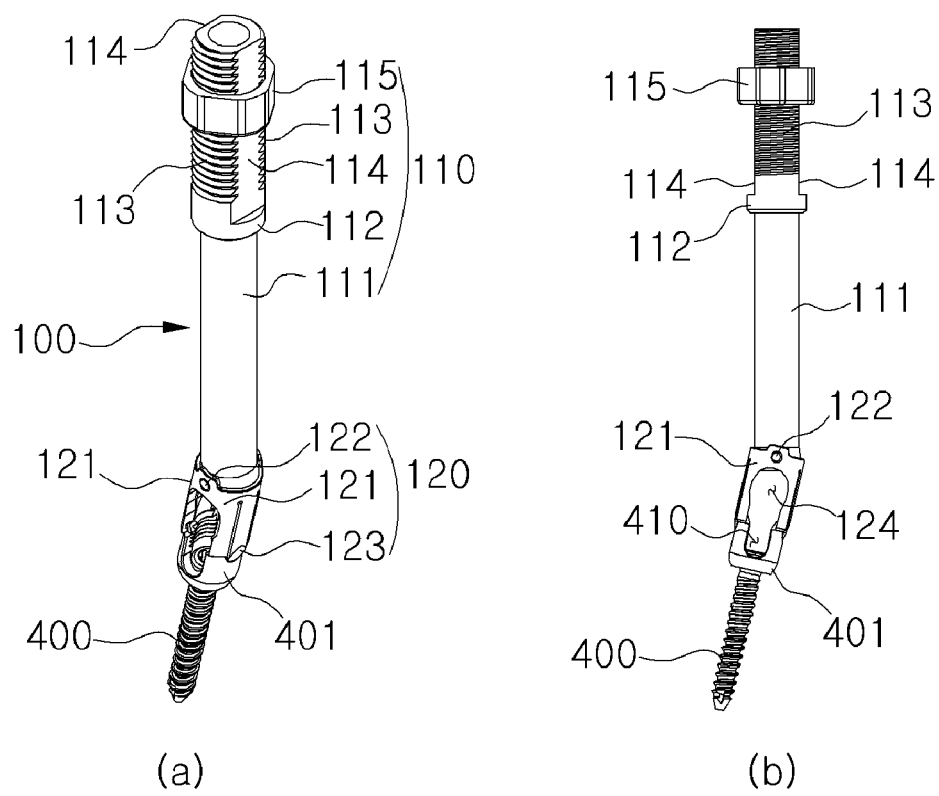
FIG. 20 is a conceptual view illustrating an overall outer appearance of an operation state of the screw holder with a joint for the minimal invasive surgery according to an embodiment, i.e., FIG. 20 panel (a) is a perspective view, and FIG. 20 panel (b) is a side view.

Also, FIG. 20 is a conceptual view illustrating an overall outer appearance of an operation state of the screw holder with a joint for the minimal invasive surgery according to an embodiment, i.e., FIG. 20 panel (a) is a perspective view, and FIG. 20 panel (b) is a side view.

Figure 21:
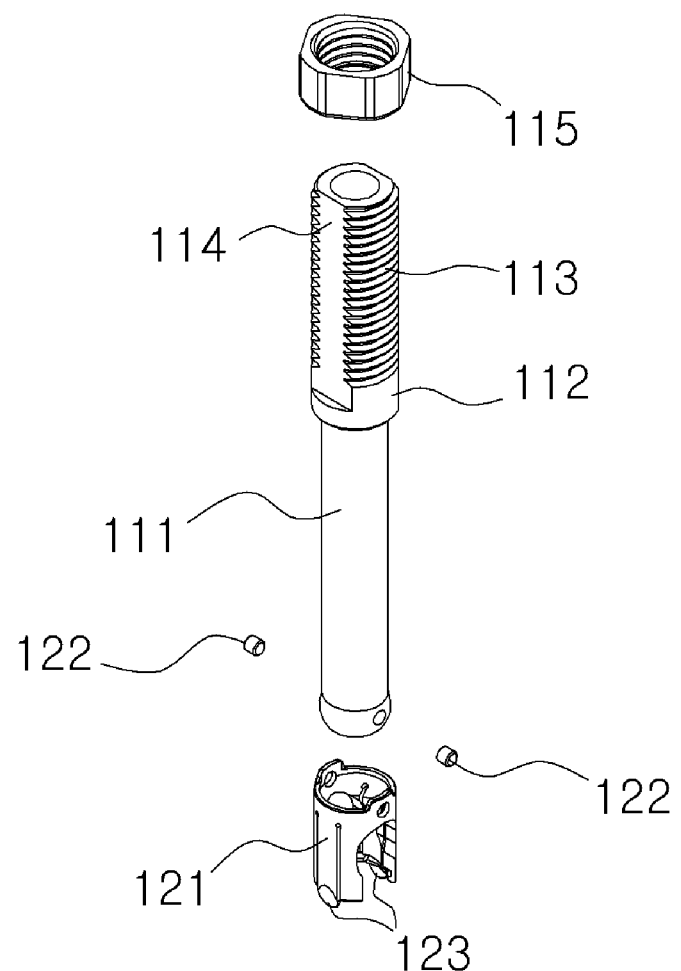
FIG. 21 is an exploded perspective view illustrating an overall coupled relationship of the screw holder with the joint for the minimal invasive surgery according to an embodiment.

Also, FIG. 21 is an exploded perspective view illustrating an overall coupled relationship of the screw holder with the joint for the minimal invasive surgery according to an embodiment.

Figure 22:
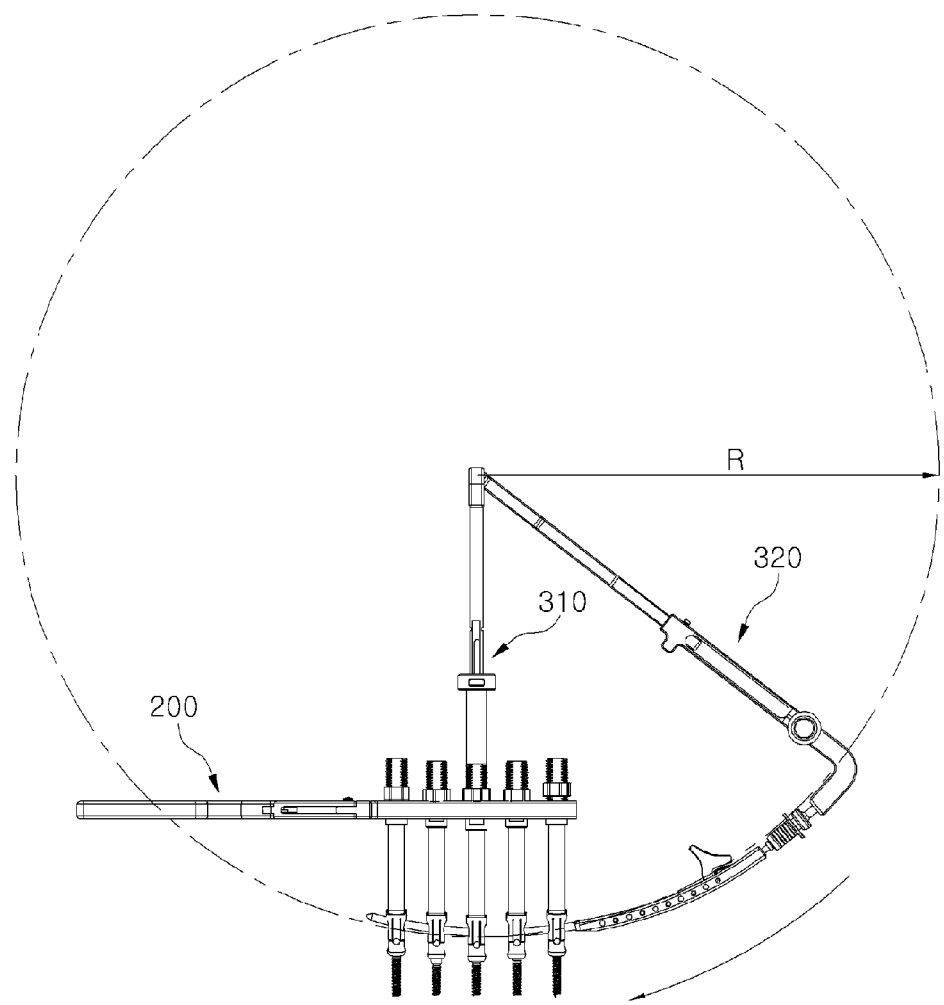
FIG. 22 is a side-conceptual view illustrating an operation state of the apparatus for the minimal invasive surgery using the screw holder with the joint for the minimal invasive surgery according to an embodiment.

Also, FIG. 22 is a side-conceptual view illustrating an operation state of the apparatus for the minimal invasive surgery using the screw holder with the joint for the minimal invasive surgery according to an embodiment.

Figure 23:
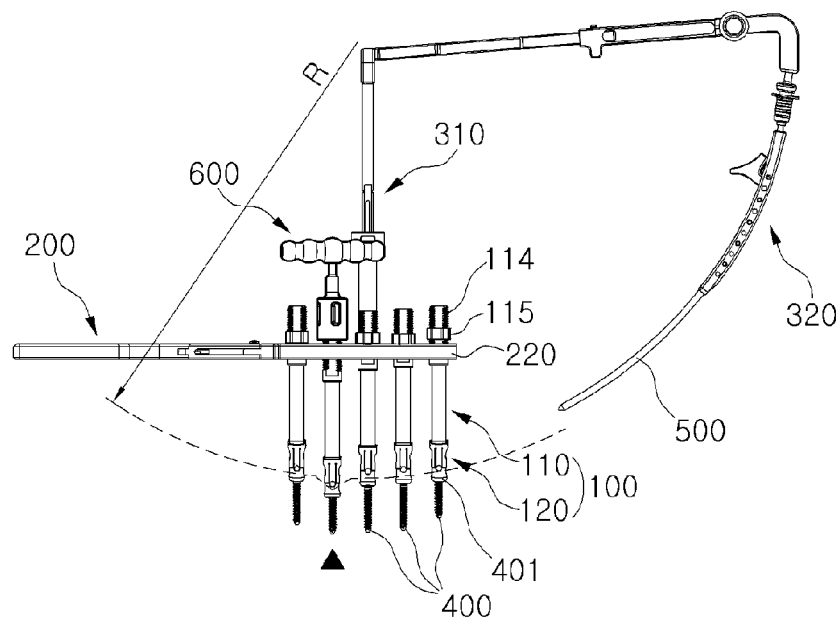
FIG. 23 is a side-conceptual view illustrating a state in which a screw reducer for the minimal invasive surgery is mounted on the apparatus for the minimal invasive surgery according to an embodiment.

Also, FIG. 23 is a side-conceptual view illustrating a state in which a screw reducer for the minimal invasive surgery is mounted on the apparatus for the minimal invasive surgery according to an embodiment.

Figure 24:
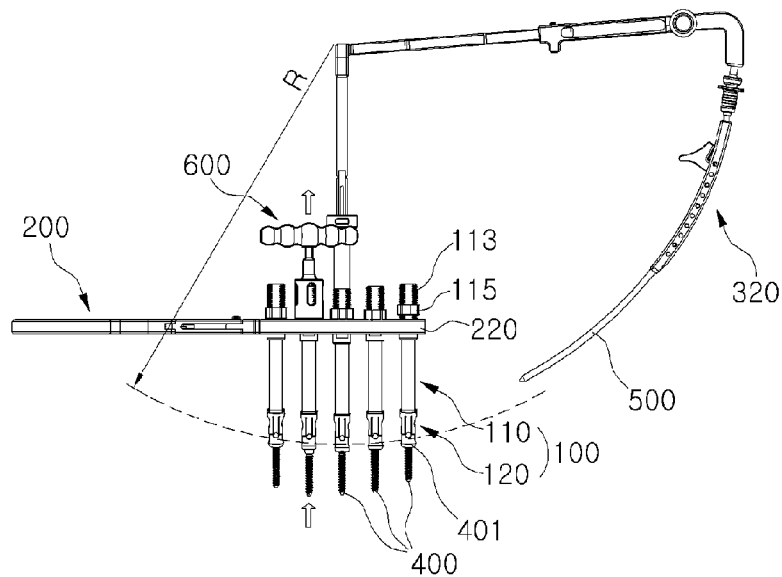
FIG. 24 is a side-conceptual view illustrating a state in which the screw reducer for the minimal invasive surgery is mounted on the apparatus for the minimal invasive surgery to form an air shape corresponding to a radius of lordosis and thereby to complete the reducing of the screw according to an embodiment.

Also, FIG. 24 is a side-conceptual view illustrating a state in which the screw reducer for the minimal invasive surgery is mounted on the apparatus for the minimal invasive surgery to form an air shape corresponding to a radius R of lordosis and thereby to complete the reducing of the screw 400 according to an embodiment.

Figure 25:
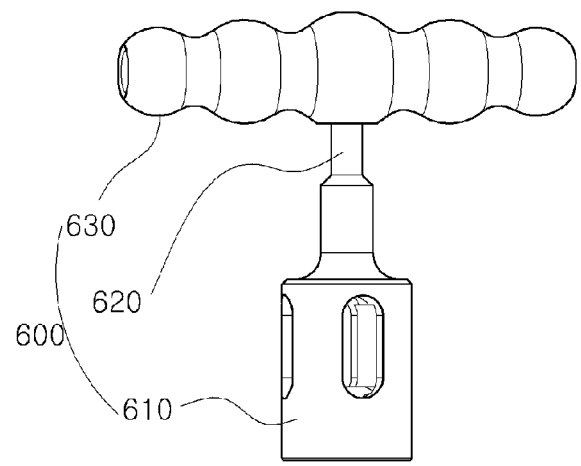
FIG. 25 is a conceptual view of the screw reducer for the minimal invasive surgery according to an embodiment.

Also, FIG. 25 is a conceptual view of the screw reducer for the minimal invasive surgery according to an embodiment.

Figure 26:
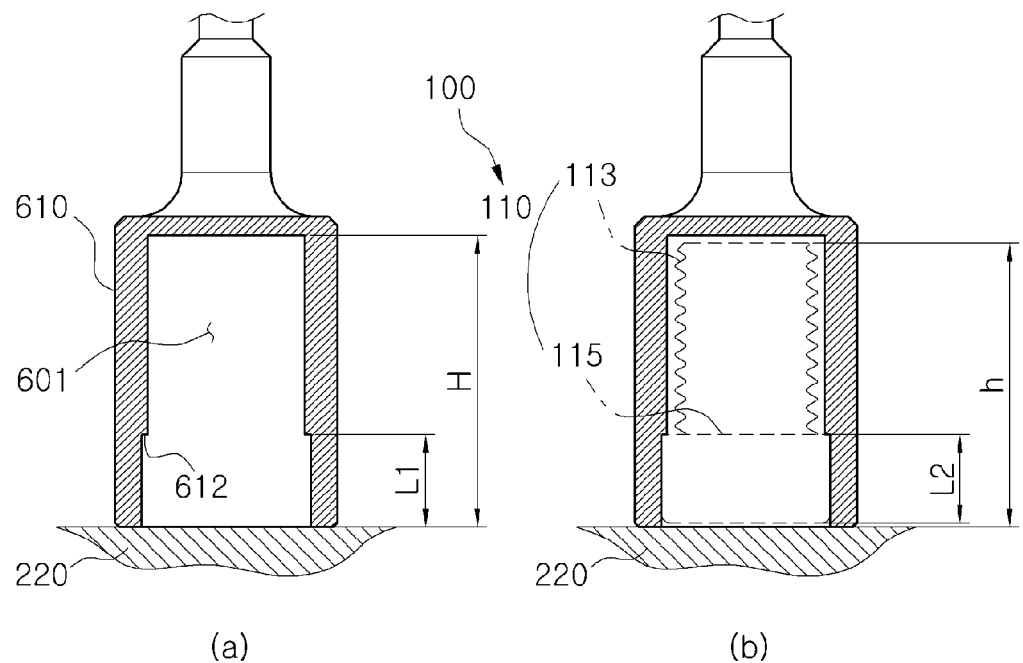
FIG. 26 is a view illustrating an inner structure of the screw reducer for minimal invasive surgery according to an embodiment, i.e., FIG. 26 panel (a) is a view illustrating an inner structure of a corrector body in a state in which a bottom surface of the corrector body contacts the clamping bar of the alignment unit, and FIG. 26 panel (b) is a partial cross-sectional conceptual view illustrating a state in which an upper portion of the holder unit is accommodated in a reducing space of the correction body, and the alignment nut is hooked and fixed to a hook protrusion.

Also, FIG. 26 is a view illustrating an inner structure of the screw reducer for minimal invasive surgery according to an embodiment, i.e., FIG. 26 panel (a) is a view illustrating an inner structure of a corrector body 610 in a state in which a bottom surface of the corrector body 610 contacts the clamping bar 220 of the alignment unit 200, and FIG. 26 panel (b) is a partial cross-sectional conceptual view illustrating a state in which an upper portion of the holder unit 100 is accommodated in a reducing space 601 of the correction body 610, and the alignment nut 115 is hooked and fixed to a hook protrusion 612.

For reference, non-explained reference numeral in FIGS. 10 to 18 will refer to FIGS. 1 to 9.

[1. Rod Inserter for Fixing Pedicle Screw and Apparatus for Minimal Invasive Surgery Using the Same]

First, it is seen that a rod inserter for fixing a pedicle screw according to an embodiment has a structure including a rotational support unit 310 and a rotational insertion unit 320 as illustrated in FIG. 1.

The rotational support unit 310 has a length corresponding to a radius of lordosis formed by lumbar of vertebrae of a subject person, and a lower end of the rotational support unit 310 is fixed to one side of an alignment unit 200 that will be described later.

The rotational insertion unit 320 has a length corresponding to the radius. Also, the rotational insertion unit 320 has one end rotatably coupled to an upper end of the rotational support unit 310 and the other end to which an arc-shaped rod 500 is detachably coupled.

Here, each of the rotational support unit 310 and the rotational insertion unit 320 may have lengths R1 and R2, which vary according to an increase or decrease of an n number in an n-level (where n is an integer equal to or greater than 1) that is in a state in which n+1 pedicle screws are respectively fixed to n+1 vertebrae. For example, each of the rotational support unit 310 and the rotational insertion unit 320 may have a length R1 in a 2-level as illustrated in FIG. 1 panel (a) and a length R2 in a 4-level as illustrated in FIG. 1 panel (b).

Thus, since each of the rotational support unit 310 and the rotational insertion unit 320 has the lengths that vary according to the increase and decrease of the level number, an operation for penetrating and inserting the arc-shaped rod 500 having various lengths and radii, which are required for the minimal invasive surgery in various cases, as one device into plurality of screws 400 to fix the rod may be smoothly performed.

The foregoing embodiment as well as following various embodiments may be applied to the present disclosure.

First, particularly, the rotational support unit 310 includes a support cylinder 311 to which a lower end of the rotational support unit 310 is fixed and an accessible rod 312 accommodated accessible through the support cylinder 311.

Also, the rotational support unit 310 includes a rotational bracket 313 disposed on an upper end of the accessible rod 312 and to which a rotational insertion unit 320 that will be described later is rotatably coupled.

Also, referring to FIGS. 2 to 5 together with FIG. 1, the rotational support unit 310 includes a first adjusting part 700 disposed on each of the support cylinder 311 and the accessible rod 312 to maintain a state in which the accessible rod 312 is withdrawn from or accommodated into the support cylinder 311.

Particularly, the first adjusting part 700 includes a first operation housing 710 disposed on an upper end of the support cylinder 311 to define an operation space therein.

Also, the first adjusting part 700 includes a first adjusting body 720 built in the first operation housing 710, having one end exposed from an outer surface of the first operation housing 710, through which the accessible rod 312 passes, and reciprocated in a direction perpendicular to an accessible direction of the accessible rod 312.

Also, the first adjusting part 700 includes a first biasing means 730 disposed between the other end of the first adjusting body 720 and an inner surface of the first operation housing 710 to generate supporting force in a direction in which the first adjusting body 720 protrudes to the outside of the first operation housing 710.

Also, the first adjusting part 700 includes a first operation control means 740 disposed on each of an outer surface of the accessible rod 312 and the first adjusting body 720 to allow or restrict the withdrawal or accommodation of the accessible rod 312 with respect to the support cylinder 311 by being engaged with the accessible rod 312 or releasing the engagement according to the reciprocation of the first adjusting body 720.

Here, the first adjusting body 720 includes a first reciprocation piece 721 through which the accessible rod 312 passes and reciprocated within the first operation housing 710.

Here, the first adjusting body 720 includes a first pushing piece 722 extending from one end of the first reciprocation piece 721 and exposed from a first access slot 711 passing through an outer surface of the first operation housing 710.

Thus, the first biasing means 730 may be disposed between the other end of the first reciprocation piece 721 and the first operation housing 710, and a portion of the first operation control means 740 may be disposed on the first reciprocation piece 721.

In more detail, the first operation control means 740 includes a first adjusting groove 741 defined in each of both sides of a circumferential surface of the accessible rod 312 and provided in plurality so that the plurality of first adjusting grooves 741 are spaced apart from each other in a vertical longitudinal direction of the accessible rod 312.

Also, the first operation control means 740 includes an access stepped surface 742 disposed on each of both sides of the circumferential surface of the accessible rod 312 in a direction perpendicular to a direction in which the plurality of first adjusting grooves 741 are defined and cut by a predetermined width and length along the vertical longitudinal direction of the accessible rod 312.

Also, the first operation control means 740 includes a first access control slot 743 defined to penetrated by a predetermined length in a direction in which the access stepped surface is disposed.

Also, the first operation control means 740 includes a first control pin (see reference numeral 744 of FIG. 11) that is coupled to the support cylinder 311 in a direction perpendicular to the access direction of the accessible rod 312 and of which an end is accommodated into the first access control slot 743.

Thus, the access stepped surface 742 of the first adjusting groove 741 may be engaged with the first adjusting body 720 or released from the engagement to allow or restrict the access of the accessible rod 312 as illustrated in FIG. 4.

Also, the first control pin 744 may allow the accessible rod 312 to be accessed within the length of the first access control slot 743 and prevent the accessible rod 312 from being separated from the support cylinder 311.

Referring to FIGS. 4 and 5, the first operation control means 740 further includes an access-allowable hole 745 penetrated with a diameter corresponding to the accessible rod 312 in the first reciprocation piece 721 of the first adjusting body 720.

Also, the first operation control means 740 further includes a first reciprocation-allowable slot 746 that is cut from an edge of the access-allowable hole 745 to the other end of the first reciprocation piece 721 contacting the first biasing means 730.

Also, the first operation control means 740 further includes a first adjusting piece 747 protruding from each of both edges of the first reciprocation-allowable slot 746 to face each other and engaged with the first adjusting groove 741.

Thus, it is seen that the access stepped surface 742 contacts the other end of the first reciprocation-allowable slot 746 in a state in which the first reciprocation piece 721 is maximally pushed to the outside of the first operation housing 710 by the first biasing means 730 as illustrated in FIG. 4 panel (a).

Particularly, the rotational insertion unit 320 includes a rotational bar 321 rotatably coupled to the upper end of the rotational support unit 310 and an accessible cylinder 322 coupled to an end of the rotational bar 321 to accommodate the rotational bar 321 so as to be assessable through the rotational bar 321 and varying in total length together with the rotational bar 321.

Also, the rotational insertion unit 320 includes a connection bracket 323 extending from an end of the accessible cylinder 322 to form a portion of the arc shape.

Also, the rotational insertion unit 320 includes an insertion guide body 324 detachably coupled to an end of the connection bracket 323 to form the rest portion of the arc shape.

Also, referring to FIGS. 6 to 9 together with FIG. 1, the rotational insertion unit 320 includes a second adjusting part 800 disposed on each of the rotational bar 321 and the accessible cylinder 322 to maintain a state in which the accessible cylinder 322 is withdrawn from or accommodated into the rotational bar 321.

Here, the arc-shaped rod 500 is detachably coupled to an end of the insertion guide body 324, and the connection bracket 323, the insertion guide body 324, and the arc-shaped rod 500 form an arc corresponding to the radius of the lordosis.

Particularly, the second adjusting part 800 includes a second operation housing 810 disposed on an upper end of the accessible cylinder 322 to define an operation space therein.

Also, the second adjusting part 800 includes a second adjusting body 820 built in the second operation housing 810, having one end exposed from an outer surface of the second operation housing 810, through which the rotational bar 321 passes, and reciprocated in a direction perpendicular to an accessible direction of the rotational bar 321.

Also, the second adjusting part 800 includes a second biasing means 830 disposed between the other end of the second adjusting body 820 and an inner surface of the second operation housing 810 to generate supporting force in a direction in which the second adjusting body 820 protrudes to the outside of the second operation housing 810.

Also, the second adjusting part 800 includes a second operation control means 840 disposed on each of the accessible cylinder 322 and an outer surface of the rotational bar 321 to allow or restrict the withdrawal or accommodation of the rotational bar 321 with respect to the accessible cylinder 322 by being engaged with the rotational bar 321 or releasing the engagement according to the reciprocation of the second adjusting body 820.

Here, the second adjusting body 820 includes a second reciprocation piece 821 through which the rotational bar 321 passes and reciprocated within the second operation housing 810.

Here, the second adjusting body 820 includes a second pushing piece 822 extending from one end of the second reciprocation piece 821 and exposed from a second access slot 811 passing through an outer surface of the second operation housing 810.

Thus, the second biasing means 830 may be disposed between the other end of the second reciprocation piece 821 and the second operation housing 810, and a portion of the second operation control means 840 may be disposed on the second reciprocation piece 821.

Particularly, the second operation control means 840 includes an access stepped part 842 that is formed to be stepped from one end to the other end of the rotational bar 321.

Also, the second operation control means 840 includes a second adjusting groove 841 defined in each of the access stepped part 842 and an outer surface of the rotational bar 321 and provided in plurality so that the plurality of second adjusting grooves 841 are spaced apart from each other in a longitudinal direction of the rotational bar 321.

Also, the second operation control means 840 includes a second access control slot 843 defined to penetrated by a predetermined length in a direction in which the rotational bar 321 is disposed.

Also, the second operation control means 840 includes a second control pin 844 that is coupled to the accessible cylinder 322 in a direction perpendicular to the access direction of the rotational bar 321 and of which an end is accommodated into the second access control slot 843.

Thus, the second adjusting groove 841 and the access stepped part 842 may be engaged with the second adjusting body 820 or released from the engagement to allow or restrict the access of the rotational bar 321 as illustrated in FIGS. 6 and 8.

Also, the second control pin 844 may allow the rotational bar 321 to be accessed within the length of the second access control slot 843 and prevent the accessible cylinder 322 from being separated from rotational bar 321.

Referring to FIGS. 8 and 9, the second operation control means 840 further includes an access-allowable slot 845 penetrated in a shape corresponding to a cross-section of the assess stepped part 842 in the second reciprocation piece 821 of the second adjusting body 820.

Also, the second operation control means 840 further includes a second reciprocation-allowable slot 846 that is cut from an edge of the access-allowable slot 845 to the other end of the second reciprocation piece 821 contacting the second biasing means 830.

Also, the second operation control means 840 further includes a second adjusting piece 847 protruding from each of both edges of the second reciprocation-allowable slot 846 to face each other and engaged with the second adjusting groove 841.

Thus, it is seen that the access stepped part 842 contacts the other end of the second reciprocation-allowable slot 846 in a state in which the second reciprocation piece 821 is maximally pushed to the outside of the second operation housing 810 by the second biasing means 830 as illustrated in FIG. 8 panel (a).

The apparatus for the minimal invasive surgery using the rod inserter for fixing the pedicle screw according to an embodiment may include the insertion unit 300 of FIGS. 1 to 9. In addition, as illustrated in FIGS. 10 and 11, the apparatus may include the holder unit 100 and the alignment unit 200.

The holder unit 100 includes a holder body 110 having both penetrated ends and a detachable part 120 rotatably coupled to an end of the holder body 110 and coupled to a head part 401 of a screw 400 fixed to the vertebra.

The alignment unit 200 may be provided for clamping upper portions of the holder bodies 110 coupled to the plurality of head parts 401 at the same time to locate the upper portions of the holder unit 100 in a straight line.

The insertion unit 300 may be disposed on one side of the alignment unit 200 and provided for penetrating and inserting the rod 500 having the arc shape corresponding to the radius (see reference symbols R1 or R2 of FIG. 1) of the lordosis formed by the lumbar of the vertebrae of the subject person into the plurality of detachable parts 120.

The insertion unit 300 includes the rotational support unit 310 of which a lower end is mounted on one side of the alignment unit 200 and the rotational insertion unit 320 having a length corresponding to the radius R1 or R2 of the lordosis, having an end to which the arc-shaped rod 500 is detachably coupled, and rotatably coupled to the upper end of the rotational support unit 310.

Thus, each of the rotational support unit 310 and the rotational insertion unit 320 may have lengths R1 and R2, which vary according to an increase or decrease of an n number in an n-level (where n is an integer equal to or greater than 1) that is in a state in which n+1 pedicle screws 400 are respectively fixed to n+1 vertebrae, as described above.

Referring to FIGS. 20 and 21, it is seen that the holder body 110 includes a support part 111 having both penetrated ends.

Also, the holder body 110 includes a stepped part 112 having a diameter greater than that of the support part 111 and disposed to be stepped on an upper portion of the support part 111.

Also, the holder body 110 includes a screw thread 113 disposed on an outer circumferential surface of the stepped part 112.

Also, the holder body 110 includes alignment contact surfaces 114 respectively disposed on both sides of an outer circumferential surface of the stepped part 112 to face each other and stepped with a predetermined length and width downward from an end of the upper end of the stepped part 112.

Here, it is seen that the detachable part 120 attached to or detached from the head part 401 is rotatably coupled to each of both sides of an outer circumferential surface of a lower end of the support part 111.

Referring to FIGS. 20 and 21, it is seen that the detachable part 120 includes a detachable body 121 having both penetrated ends.

Also, the detachable part 120 includes a rotational pin 122 coupled to be penetrated and coupled to both sides of an edge of an upper end of the detachable body 121 and fixed to both sides of an outer circumferential surface of a lower end of the support part 111.

Also, the detachable part 120 includes a detachable protrusion piece 123 disposed on both sides of an edge of a lower end of the detachable body 121 and hooked and fixed to both sides of an outer circumferential surface of an upper end of the head part 401.

Also, the detachable part 120 includes rod insertion guide grooves 124 that are cut upward from both sides of the edge of the lower end of the detachable body 121 to face each other and communicate with rod insertion grooves 410 that are cut downward from both sides of the outer circumferential surface of the upper end of the head part 401 to face each other.

Thus, the rod 500 having the arc shape corresponding to the radius R1 or R2 of the lordosis formed by the lumbar of the vertebrae of the subject person may pass to be inserted into each of the rod insertion guide grooves 124 and the rod insertion grooves 410.

That is, the rod insertion guide grooves 124 may be provided for guiding the coupling of the arc-shaped rod 500 coupled to pass through the head part 401 fixed to each of the plurality of vertebrae.

Here, the plurality of vertebrae may be 2 or more. Also, the screw holder for the minimal invasive surgery may be applied to the minimal invasive surgery having a 3-level or more in addition to the 1-level and the 2-level, as described above.

Here, an n-level (n is an integer equal to or greater than 1) denotes a state in which n+1 screws 400 are respectively fixed to n+1 vertebrae.

Figure 19:
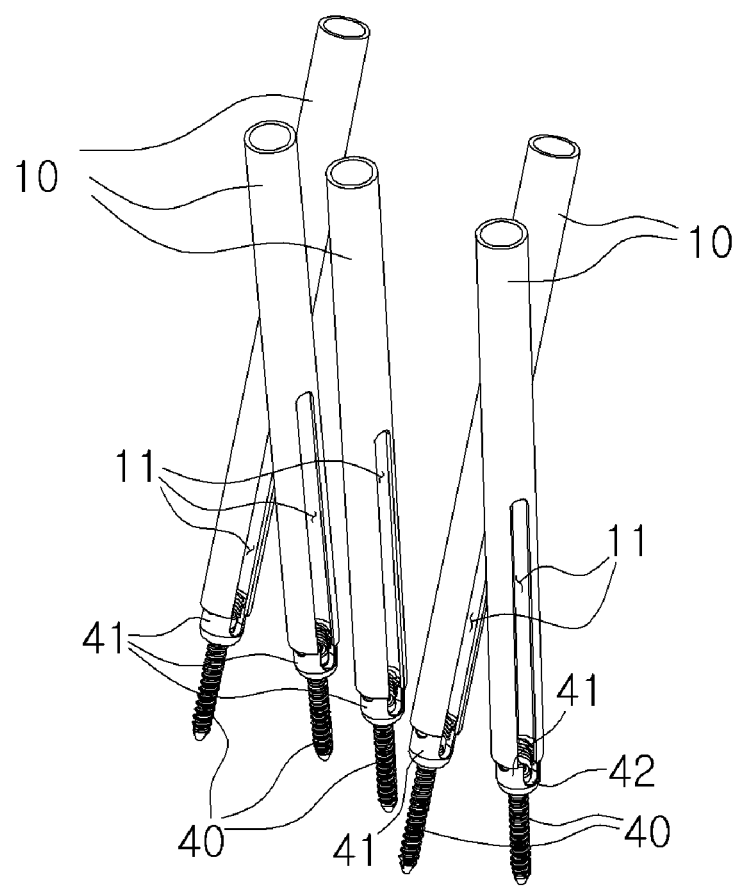
FIG. 19 is a perspective view illustrating a state in which a screw holder for a minimal invasive surgery and a pedicle screw are coupled to each other according to the related art.

That is, since the detachable part 120 is rotatable with respect to the holder body 110, in case of the 3-level (four screws 400 are inserted) or more in the existing apparatus for the minimal invasive surgery, a fatal limitation in which the screw holder (see reference numeral 40 of FIG. 19) is separated from the head (see reference numeral 42 of FIG. 19) while the operator forcibly or manually inserts the rod, or the insertion device such as the rod inserter is used may be previously prevented.

The holder body 110 may further include an alignment nut 115 engaged with the screw thread 113 and coupled to the stepped part 112 so that the upper portions of the plurality of holder bodies 110 are aligned in a straight line on the alignment unit 200 that will be described later.

Also, as illustrated in FIGS. 10 and 11, the detachable part 120 may be rotatable to correspond to tilted angles different from each other, at which the head parts 401 of the screws 400 respectively fixed to the plurality of vertebrae including a vertebra and vertebrae adjacent thereto are respectively angled with respect to the plurality of vertebrae.

More particularly, the alignment unit 200 includes a pair of grip parts 210 that are rotatable with respect to a clamping shaft 201.

Also, the alignment unit 200 includes clamping bars 220 respectively extending from the pair of grip parts 210, spread with respect to each other while moving in a direction in which the pair of grip parts 210 approach each other, moving in a direction in which the pair of grip parts 210 contact each other when force applied to the pair of grip parts 210 is removed, and clamping the upper portions of the plurality of holder bodies 110 at the same time.

It is seen that the insertion unit 300 is coupled to an outer surface of one clamping bar 220 of the pair of clamping bars 220.

Also, the alignment unit 200 may further include link bars 230 having both rotatable ends to correspond to a diameter of the stepped part 112 of the holder unit 100 and distances between the alignment contact surfaces 114, which vary whenever the operation is performed.

That is, the link bars 230 are disposed between the pair of grip parts 210 and the pair of clamping bars 220 and have both ends that are respectively rotatable with respect to the pair of grip parts 210 and the pair of clamping bars 220.

Hereinafter, a process of performing the minimal invasive surgery by using the rod inserter for fixing the pedicle screw and the apparatus for the minimal invasive surgery using the same will be briefly described with respect to FIGS. 12 to 15.

First, as illustrated in FIG. 12, the operator allows the clamping bars 220 of the alignment unit 200 to approach the alignment contact surface 114 of the holder unit 100 in a state in which the screws 400 are respectively fixed to the plurality of vertebrae.

Thereafter, the operator allows the clamping bars 220 to contact the alignment contact surface 114 and reduce the alignment nut 115 in an arrow direction along the screw thread 113 of the holder unit 100 as illustrated in FIG. 13 to align the alignment nuts 115 with each other on an edge of an upper portion of the clamping bars 220 as illustrated in FIG. 14.

Successively, the operator couples the insertion unit 300 to the alignment unit 200 as illustrated in FIG. 15 to insert the arc-shaped rod 500 in the arrow direction.

As illustrated in FIGS. 16 to 18, the rotational insertion unit 320 together with the rotational support unit 310 may be applied to an embodiment in which the operator directly performs the operation by using sense of operator own hands, instead of the structure including the rotational bar 321, the accessible cylinder 322, the connection bracket 323, and the insertion guide body 324.

That is, the operator may perform the operation by using only the insertion guide body 324 so that the arc-shaped rod 500 is directly inserted through the rod insertion guide groove 124 of the detachable part 120 that is rotated to be bent from the end of each of the holder bodies 110 aligned in the straight line by the alignment unit 200.

That is, the rotational insertion unit 320 may couple the arc-shaped rod 500 by using only the insertion guide body 324 instead of the rotation force of the rotational insertion unit 320 with respect to the rotational support unit 310 to perform the operation in such a manner in which the arc-shaped rod 500 is pushed through the opening formed by cutting the body of the subject person to perform the minimal invasive surgery.

For this, the rotational insertion unit 320 may insert the arc-shaped rod 500 into each of the plurality of detachable parts 120 as illustrated in FIG. 18 in a state in which the handle 326 for the manual insertion is detachably coupled to the connection end with the connection bracket 323 in the insertion guide body 324 as illustrated in FIG. 17 so that the operator directly grapes and inserts the rod.

As described above, the technical ideas of the present disclosure is to provide the rod inserter for fixing the pedicle screw through the arc-shaped rods having lengths different from each other are coupled according to the number of screws that are respectively fixed to the vertebrae of the subject person as one device to perform the operation and the apparatus for the minimal invasive surgery using the same.

[2. Screw Holder with Joint for Minimal Invasive Surgery and Apparatus for Minimal Invasive Surgery Using the Same]

First, as illustrated in FIGS. 20 and 21, a screw holder with a joint for a minimal invasive surgery according to an embodiment includes a holder body 110 having both penetrated ends and a detachable part 120 rotatably coupled to an end of the holder body 110 and coupled to a head part 401 of a screw 400 fixed to a vertebra (now shown).

Here, the screw 400 may be rotatable with respect to the head part 401, and the detachable part 120 may communicate with the head part 401 through the holder body 110.

Here, a driver for fixing the screw 400, which fixes the screw 400 to the vertebra, is inserted into the head part 401 via the holder body 110 and the detachable part 120 to rotate and fix the screw 400 to the vertebra.

Thus, each of the head part 401 of each of the screws respectively fixed to the vertebrae may be quickly and easily fixed at a time by using one rod having an arc shape corresponding to lordosis of a subject person through a structure in which the detachable part 120 is rotatably coupled to the holder body 110 having both penetrated ends.

The foregoing embodiment as well as following various embodiments may be applied to the present disclosure.

Referring to FIGS. 20 and 21, it is seen that the holder body 110 includes a support part 111 having both penetrated ends.

Also, the holder body 110 includes a stepped part 112 having a diameter greater than that of the support part 111 and disposed to be stepped on an upper portion of the support part 111.

Also, the holder body 110 includes a screw thread 113 disposed on an outer circumferential surface of the stepped part 112.

Also, the holder body 110 includes alignment contact surfaces 114 respectively disposed on both sides of an outer circumferential surface of the stepped part 112 to face each other and stepped with a predetermined length and width downward from an end of an upper end of the stepped part 112.

Here, it is seen that the detachable part 120 attached to or detached from the head part 401 is rotatably coupled to each of both sides of an outer circumferential surface of a lower end of the support part 111.

Referring to FIGS. 20 and 21, it is seen that the detachable part 120 includes a detachable body 121 having both penetrated ends.

Also, the detachable part 120 includes a rotational pin 122 coupled to be penetrated and coupled to both sides of an edge of an upper end of the detachable body 121 and fixed to both sides of the outer circumferential surface of the lower end of the support part 111.

Also, the detachable part 120 includes a detachable protrusion piece 123 disposed on both sides of an edge of a lower end of the detachable body 121 and hooked and fixed to both sides of an outer circumferential surface of an upper end of the head part 401.

Also, the detachable part 120 includes rod insertion guide grooves 124 that are cut upward from both sides of the edge of the lower end of the detachable body 121 to face each other and communicate with rod insertion grooves 410 that are cut downward from both sides of the outer circumferential surface of the upper end of the head part 401 to face each other.

Thus, the rod 500 having the arc shape corresponding to a radius (see reference symbol R1 of FIG. 22) of the lordosis formed by the lumbar of the vertebrae of the subject person may pass to be inserted into each of the rod insertion guide grooves 124 and the rod insertion grooves 410.

That is, the rod insertion guide grooves 124 may be provided for guiding the coupling of the arc-shaped rod 500 coupled to pass through the head part 401 fixed to each of the plurality of vertebrae.

Here, the plurality of vertebrae may be 2 or more. Also, the screw holder for the minimal invasive surgery may be applied to the minimal invasive surgery having a 3-level or more in addition to the 1-level and the 2-level.

Here, an n-level (n is an integer greater than 1) denotes a state in which n+1 screws 400 are respectively fixed to n+1 vertebrae.

That is, since the detachable part 120 is rotatable with respect to the holder body 110, in case of the 3-level (four screws 400 are inserted) or more in the existing apparatus for the minimal invasive surgery, a fatal limitation in which the screw holder (see reference numeral 40 of FIG. 19) is separated from the head (see reference numeral 42 of FIG. 19) while the operator forcibly or manually inserts the rod, or the insertion device such as the rod inserter is used may be previously prevented.

The holder body 110 may further include an alignment nut 115 engaged with the screw thread 113 and coupled to the stepped part 112 so that the upper portions of the plurality of holder bodies 110 are aligned in a straight line on the alignment unit 200 that will be described later.

Also, as illustrated in FIG. 10, the detachable part 120 may be rotatable to correspond to tilted angles different from each other, at which the head parts 401 of the screws 400 respectively fixed to the plurality of vertebrae including a vertebra and vertebrae adjacent thereto are respectively angled with respect to the plurality of vertebrae.

The apparatus for the minimal invasive surgery using the screw holder with the joint for the minimal invasive surgery having the above-described structure will be described below.

The apparatus for the minimal invasive surgery using the screw holder with the joint for the minimal invasive surgery according to an embodiment may include a holder unit 100, an alignment unit 200, and an insertion unit 300 as illustrated in FIGS. 10, 12, and 22.

First, the holder unit 100 includes a holder body 110 having both penetrated ends and a detachable part 120 rotatably coupled to an end of the holder body 110 and coupled to a head part 401 of a screw 400 fixed to the vertebra.

Also, the alignment unit 200 may be provided for clamping upper portions of the holder bodies 110 coupled to the plurality of head parts 401 at the same time to locate the upper portions of the holder unit 100 in a straight line.

Also, the insertion unit 300 may be disposed on one side of the alignment unit 200 and provided for penetrating and inserting the rod 500 having the arc shape corresponding to the radius R1 of the lordosis formed by the lumbar of the vertebrae of the subject person into the plurality of detachable parts 120.

More particularly, the alignment unit 200 includes a pair of grip parts 210 that are rotatable with respect to a clamping shaft 201.

Also, the alignment unit 200 includes clamping bars 220 respectively extending from the pair of grip parts 210, spread with respect to each other while moving in a direction in which the pair of grip parts 210 approach each other, moving in a direction in which the pair of grip parts 210 contact each other when force applied to the pair of grip parts 210 is removed, and clamping the upper portions of the plurality of holder bodies 110 at the same time.

Thus, it is seen that the insertion unit 300 is coupled to an outer surface of one clamping bar 220 of the pair of clamping bars 220.

Also, it is seen that surfaces facing each other of the pair of clamping bars 220 respectively contact the alignment contact surfaces 114.

Also, the alignment unit 200 may further include link bars 230 having both rotatable ends to correspond to a diameter of the stepped part 112 of the holder unit 100 and distances between the alignment contact surfaces 114, which vary whenever the operation is performed.

That is, the link bars 230 are disposed between the pair of grip parts 210 and the pair of clamping bars 220 and have both ends that are respectively rotatable with respect to the pair of grip parts 210 and the pair of clamping bars 220.

The insertion unit 300 includes the rotational support unit 310 of which a lower end is mounted on one side of the alignment unit 200 and the rotational insertion unit 320 having a length corresponding to the radius R1 of the lordosis, having an end to which the arc-shaped rod 500 is detachably coupled, and rotatably coupled to the upper end of the rotational support unit 310.

Thus, as illustrated in FIG. 22, the arc-shaped rod 500 may be inserted to pass through each of the detachable parts 120 that are rotatably coupled to the holder body 110 by the rotation of the rotational insertion unit 320.

Also, the rotational support unit 310 may vary in length to correspond to various body types of subject persons and the radius R of the lordosis formed by the lumbar of the vertebrae of the subject person.

For this, the rotational support unit 310 may include a support cylinder 311, an accessible rod 312, and a rotational bracket 313.

The support cylinder 311 is inserted into and fixed to a fixed bracket 221 disposed on an outer surface of one clamping bar 220 of the pair of clamping bars 220 of the alignment unit 200.

The accessible rod 312 is accommodated accessible through the support cylinder 311.

The rotational bracket 313 is disposed on an upper end of the accessible rod 312 and to which an upper end of the rotational insertion unit 320 is rotatably coupled.

Also, the rotational insertion unit 320 may vary in length to correspond to various body types of subject persons and the radius R of the lordosis formed by the lumbar of the vertebrae of the subject person.

For this, the rotational insertion unit 320 may include a rotational bar 321, an accessible cylinder 322, a connection bracket 323, and an insertion guide body 324.

The rotational bar 321 is rotatably coupled to an upper end of the rotational support unit 310.

The accessible cylinder 322 is coupled to an end of the rotational bar 321 to accommodate the rotational bar 321 so as to be accessible through the rotational bar 321 and varies in total length together with the rotational bar 321.

Also, the connection bracket 323 extends from an end of the accessible cylinder 322 to form a portion of the arc shape.

Also, the insertion guide body 324 is detachably coupled to an end of the connection bracket 323 to form the rest portion of the arc shape.

Thus, the arc-shaped rod 500 is detachably coupled to an end of the insertion guide body 324, and the connection bracket 323, the insertion guide body 324, and the arc-shaped rod 500 form an arc constituting a circle (a dotted portion of FIG. 22) corresponding to the radius R of the lordosis.

Also, in the rotational insertion unit 320, the rotational bar 321 is rotated with respect to the upper end of the rotational support unit 310. Also, the rotational insertion unit 320 may further include a handle 325 that is disposed on the connection bracket 323 and is grasped by the operator so that force is applied to a direction approaching the rotational support unit 310.

Hereinafter, a process of performing the minimal invasive surgery by using the apparatus for the minimal invasive surgery using the screw holder with the joint for the minimal invasive surgery same will be briefly described with respect to FIGS. 12 to 15.

First, the operator allows the clamping bars 220 of the alignment unit 200 to approach the alignment contact surface 114 of the holder unit 100 in a state in which the screws 400 are respectively fixed to the plurality of vertebrae as illustrated in FIG. 12.

Thereafter, the operator allows the clamping bars 220 to contact the alignment contact surface 114 and reduce the alignment nut 115 in an arrow direction along the screw thread 113 of the holder unit 100 as illustrated in FIG. 13 to align the alignment nuts 115 with each other on an edge of an upper portion of the clamping bars 220 as illustrated in FIG. 14.

Successively, the operator couples the insertion unit 300 to the alignment unit 200 as illustrated in FIG. 15 to insert the arc-shaped rod 500 in an arrow direction.

As illustrated in FIGS. 16 to 18, the rotational insertion unit 320 together with the rotational support unit 310 may be applied to an embodiment in which the operator directly performs the operation by using sense of operator own hands, instead of the structure including the rotational bar 321, the accessible cylinder 322, the connection bracket 323, and the insertion guide body 324.

That is, the operator may perform the operation by using only the insertion guide body 324 so that the arc-shaped rod 500 is directly inserted through the rod insertion guide groove 124 of the detachable part 120 that is rotated to be bent from the end of each of the holder bodies 110 aligned in the straight line by the alignment unit 200.

That is, the rotational insertion unit 320 may couple the arc-shaped rod 500 by using only the insertion guide body 324 instead of the rotation force of the rotational insertion unit 320 with respect to the rotational support unit 310 to perform the operation in such a manner in which the arc-shaped rod 500 is pushed through the opening formed by cutting the body of the subject person to perform the minimal invasive surgery.

For this, the rotational insertion unit 320 may insert the arc-shaped rod 500 into each of the plurality of detachable parts 120 as illustrated in FIG. 18 in a state in which the handle 326 for the manual insertion is detachably coupled to the connection end with the connection bracket 323 in the insertion guide body 324 as illustrated in FIG. 17 so that the operator directly grapes and inserts the rod.

As described above, the technical ideas of the present disclosure is to provide the screw holder with the joint for the minimal invasive surgery, which is capable of quickly and easily fixing the head part of each of the screws fixed to a relatively large number of vertebrae at a time by using one rod corresponding to the lordosis of the subject person and the apparatus for the minimal invasive surgery using the same.

[3. Screw Reducer for Minimal Invasive Surgery and Apparatus for Minimal Invasive Surgery Using the Same]

First, a screw reducer for a minimal invasive surgery according to an embodiment may have a structure including a corrector 600 that reduces a screw 400 (screw disposed at a portion expressed by '▲' in FIG. 23) disposed at a height misaligned with a radius R of lordosis formed by lumbar among a plurality of screws 400 respectively fixed to the plurality of vertebrae that form the lumbar of the vertebrae of the subject person to form an arc shape corresponding to the radius R of the lordosis as illustrated in FIGS. 23 to 26.

Thus, the present disclosure may help generation of the adequate radius R of the lordosis before the arc-shaped rod 500 is inserted so that the arc-shaped rod 500 is smoothly inserted.

The foregoing embodiment as well as following various embodiments may be applied to the present disclosure.

First, as illustrated in FIGS. 23 and 24, the apparatus may further include a detachable part 120 having both penetrated ends, which is coupled to a head part 401 coupled to an upper end of a screw 400, a holder body 110 coupled to an upper end of the detachable part 120 so that the detachable part 120 is rotatable, and a holder unit 100 including an alignment unit 115 coupled to a screw thread 113 disposed on an upper portion of the holder body 110.

Also, the apparatus may further include an alignment unit 200 that is provided for clamping upper portions of the holder bodies 110 respectively coupled to the plurality of head parts 401 at the same time to locate the upper portions of the holder unit 100 in a straight line.

Thus, the screw 400 disposed at the misaligned height may be reduced by the corrector 600 coupled to the alignment nut 115 in a state in which the plurality of holder units 100 are disposed in a straight line by the alignment unit 200.

Referring to FIGS. 25 and 26, the corrector 600 includes a correction body 610 having an opened bottom surface to form a reducing space 601.

Also, the corrector 600 includes a hook protrusion 612 disposed upward from a lower end of an inner surface of the correction body 610 and stepped in a shape corresponding to that of an outer surface of the alignment nut 115 coupled to the screw thread 113 disposed on an upper portion of the holder unit 100 that is detachably disposed on the head part 401 coupled to an upper end of the screw 400.

Thus, the screw 400 disposed at the misaligned height may be reduced as illustrated in FIG. 24 as the correction body 610 coupled to the alignment nut 115 is rotated in place in a state in which the plurality of holder units 100 are aligned in a straight line as illustrated in FIG. 23.

A height L1 of the hook protrusion 612, which is defined from a bottom surface of the correction body 610 may be equal to or greater than that L2 of the alignment nut 115 so that the reducing is capable of being performed in a state in which the alignment nut 115 is firmly seated and fixed to the hook protrusion 612.

Here, a distance H from the bottom surface of the correction body 610 to a top surface of the inside of the reducing space 601 may be greater than that h by which an upper portion of the holder unit 100 coupled to an upper end of the screw 400 disposed at the misaligned height protrudes from the alignment nut 115 so that the state in which the alignment nut 115 is fixed to the hook protrusion 612 is securely maintained although the entire upper portion of the holder unit 100 is reduced from the state of FIG. 23 to the state of FIG. 24.

The corrector 600 may further include a support shaft 620 extending from a top surface of the correction body 610 and a rotational handle 630 disposed on an upper end of the support shaft 620 to provide convenience to the operator in reducing the screw 400 disposed at the misaligned position.

Here, the support shaft 620 and the rotational handle 630 are integrally rotated together with the correction body 610.

The apparatus for the minimal invasive surgery using the screw reducer for the minimal invasive surgery according to an embodiment may have a structure including the corrector 600 of FIGS. 23 to 26 and the holder unit 100 and the alignment unit 200 of FIGS. 10 and 11.

The holder unit 100 includes a detachable part 120 having both penetrated ends, which is coupled to a head part 401, a holder body 110 coupled to an upper end of the detachable part 120 so that the detachable part 120 is rotatable, and an alignment nut 115 coupled to the screw thread 113 disposed on the upper portion of the holder body 110.

The alignment unit 200 may be provided for clamping upper portions of the holder bodies 110 coupled to the plurality of head parts 401 at the same time to locate the upper portions of the holder unit 100 in a straight line.

Thus, the screw 400 disposed at the misaligned height may be reduced by the corrector 600 coupled to the alignment nut 115 in a state in which the plurality of holder units 100 are disposed in a straight line by the alignment unit 200.

Referring to FIG. 20, it is seen that the holder body 110 includes support part 111 having both penetrated ends.

Also, the holder body 110 includes a stepped part 112 having a diameter greater than that of the support part 111 and disposed to be stepped on an upper portion of the support part 111.

Also, the holder body 110 includes the screw thread 113 disposed on an outer circumferential surface of the stepped part 112.

Also, the holder body 110 includes alignment contact surfaces 114 respectively disposed on both sides of an outer circumferential surface of the stepped part 112 to face each other and stepped with a predetermined length and width downward from an end of an upper end of the stepped part 112.

Here, it is seen that the detachable part 120 attached to or detached from the head part 401 is rotatably coupled to each of both sides of an outer circumferential surface of a lower end of the support part 111.

Referring to FIG. 20, it is seen that the detachable part 120 includes a detachable body 121 having both penetrated ends.

Also, the detachable part 120 includes a rotational pin 122 coupled to be penetrated and coupled to both sides of an edge of an upper end of the detachable body 121 and fixed to both sides of the outer circumferential surface of the lower end of the support part 111.

Also, the detachable part 120 includes a detachable protrusion piece 123 disposed on both sides of an edge of a lower end of the detachable body 121 and hooked and fixed to both sides of an outer circumferential surface of an upper end of the head part 401.

Also, the detachable part 120 includes rod insertion guide grooves 124 that are cut upward from both sides of the edge of the lower end of the detachable body 121 to face each other and communicate with rod insertion grooves 410 that are cut downward from both sides of the outer circumferential surface of the upper end of the head part 401 to face each other.

Thus, the rod 500 having the arc shape corresponding to the radius R of the lordosis formed by the lumbar of the vertebrae of the subject person may pass to be inserted into each of the rod insertion guide grooves 124 and the rod insertion grooves 410.

That is, the rod insertion guide grooves 124 may be provided for guiding the coupling of the arc-shaped rod 500 coupled to pass through the head part 401 fixed to each of the plurality of vertebrae.

Here, the plurality of vertebrae may be 2 or more. Also, the screw holder for the minimal invasive surgery may be applied to the minimal invasive surgery having a 3-level or more in addition to the 1-level and the 2-level.

Here, an n-level (n is an integer greater than 1) denotes a state in which n+1 screws 400 are respectively fixed to n+1 vertebrae.

That is, since the detachable part 120 is rotatable with respect to the holder body 110, in case of the 3-level (four screws 400 are inserted) or more in the existing apparatus for the minimal invasive surgery, a fatal limitation in which the screw holder (see reference numeral 40 of FIG. 19) is separated from the head (see reference numeral 42 of FIG. 19) while the operator forcibly or manually inserts the rod, or the insertion device such as the rod inserter is used may be previously prevented.

The holder body 110 may further include an alignment nut 115 engaged with the screw thread 113 and coupled to the stepped part 112 so that the upper portions of the plurality of holder bodies 110 are aligned in a straight line on the alignment unit 200 that will be described later.

Also, as illustrated in FIGS. 10 and 11, the detachable part 120 may be rotatable to correspond to tilted angles different from each other, at which the head parts 401 of the screws 400 respectively fixed to the plurality of vertebrae including a vertebra and vertebrae adjacent thereto are respectively angled with respect to the plurality of vertebrae.

More particularly, the alignment unit 200 includes a pair of grip parts 210 that are rotatable with respect to a clamping shaft 201.

Also, the alignment unit 200 includes clamping bars 220 respectively extending from the pair of grip parts 210, spread with respect to each other while moving in a direction in which the pair of grip parts 210 approach each other, moving in a direction in which the pair of grip parts 210 contact each other when force applied to the pair of grip parts 210 is removed, and clamping the upper portions of the plurality of holder bodies 110 at the same time.

Thus, the corrector 600 has a bottom surface facing an edge of an upper portion of each of the clamping bars 220. As the corrector 600 coupled to the alignment nut 115 is rotated in place, the screw 400 disposed at the misaligned height, the head part 401, the detachable part 120, and the holder body 110 are integrally reduced.

Also, the alignment unit 200 may further include link bars 230 having both rotatable ends to correspond to a diameter of the stepped part 112 of the holder unit 100 and distances between the alignment contact surfaces 114, which vary whenever the operation is performed.

That is, the link bars 230 are disposed between the pair of grip parts 210 and the pair of clamping bars 220 and have both ends that are respectively rotatable with respect to the pair of grip parts 210 and the pair of clamping bars 220.

The alignment unit 200 further include an insertion unit 300 coupled to an outer surface of one clamping bar 220 of the pair of clamping bars 200 to penetrate and insert the rod 500 having the arc shape corresponding to the radius R of the lordosis formed by the lumbar of the vertebrae of the subject person into the plurality of detachable parts 120.

Here, the insertion unit 300 includes the rotational support unit 310 of which a lower end is mounted on one side of the alignment unit 200 and the rotational insertion unit 320 having a length corresponding to the radius R1 of the lordosis, having an end to which the arc-shaped rod 500 is detachably coupled, and rotatably coupled to the upper end of the rotational support unit 310.

Thus, the arc-shaped rod 500 may be inserted to pass through each of the detachable parts 120 that are rotatably coupled to the holder body 110 by the rotation of the rotational insertion unit 320 (see FIG. 15).

Also, the rotational support unit 310 may vary in length to correspond to various body types of subject persons and the radius R of the lordosis formed by the lumbar of the vertebrae of the subject person.

For this, the rotational support unit 310 may include a support cylinder 311, an accessible rod 312, and a rotational bracket 313.

The support cylinder 311 is inserted into and fixed to a fixed bracket 221 disposed on an outer surface of one clamping bar 220 of the pair of clamping bars 220 of the alignment unit 200.

The accessible rod 312 is accommodated accessible through the support cylinder 311.

The rotational bracket 313 is disposed on an upper end of the accessible rod 312 and to which an upper end of the rotational insertion unit 320 is rotatably coupled.

Also, the rotational insertion unit 320 may vary in length to correspond to various body types of subject persons and the radius R of the lordosis formed by the lumbar of the vertebrae of the subject person.

For this, the rotational insertion unit 320 may include a rotational bar 321, an accessible cylinder 322, a connection bracket 323, and an insertion guide body 324.

The rotational bar 321 is rotatably coupled to an upper end of the rotational support unit 310.

The accessible cylinder 322 is coupled to an end of the rotational bar 321 to accommodate the rotational bar 321 so as to be accessible through the rotational bar 321 and varies in total length together with the rotational bar 321.

Also, the connection bracket 323 extends from an end of the accessible cylinder 322 to form a portion of the arc shape.

Also, the insertion guide body 324 is detachably coupled to an end of the connection bracket 323 to form the rest portion of the arc shape.

Thus, the arc-shaped rod 500 is detachably coupled to an end of the insertion guide body 324, and the connection bracket 323, the insertion guide body 324, and the arc-shaped rod 500 form the arc shape (a dotted portion of FIG. 24) corresponding to the radius R of the lordosis.

Also, in the rotational insertion unit 320, the rotational bar 321 is rotated with respect to the upper end of the rotational support unit 310. Also, the rotational insertion unit 320 may further include a handle 325 that is disposed on the connection bracket 323 and is grasped by the operator so that force is applied to a direction approaching the rotational support unit 310.

Hereinafter, the screw reducer for the minimal invasive surgery and a process of performing the minimal invasive surgery by using the apparatus for the minimal invasive surgery using the same will be briefly described with respect to FIGS. 12 to 15.

First, the operator allows the clamping bars 220 of the alignment unit 200 to approach the alignment contact surface 114 of the holder unit 100 in a state in which the screws 400 are respectively fixed to the plurality of vertebrae.

Thereafter, the operator allows the clamping bars 220 to contact the alignment contact surface 114 and reduce the alignment nut 115 in an arrow direction along the screw thread 113 of the holder unit 100 as illustrated in FIG. 13 to align the alignment nuts 115 with each other on an edge of an upper portion of the clamping bars 220 as illustrated in FIG. 14.

Successively, the operator couples the insertion unit 300 to the alignment unit 200 as illustrated in FIG. 15 to insert the arc-shaped rod 500 in an arrow direction.

As illustrated in FIGS. 16 to 18, the rotational insertion unit 320 together with the rotational support unit 310 may be applied to an embodiment in which the operator directly performs the operation by using sense of operator own hands, instead of the structure including the rotational bar 321, the accessible cylinder 322, the connection bracket 323, and the insertion guide body 324.

That is, the operator may perform the operation by using only the insertion guide body 324 so that the arc-shaped rod 500 is directly inserted through the rod insertion guide groove 124 of the detachable part 120 that is rotated to be bent from the end of each of the holder bodies 110 aligned in the straight line by the alignment unit 200.

That is, the rotational insertion unit 320 may couple the arc-shaped rod 500 by using only the insertion guide body 324 instead of the rotation force of the rotational insertion unit 320 with respect to the rotational support unit 310 to perform the operation in such a manner in which the arc-shaped rod 500 is pushed through the opening formed by cutting the body of the subject person to perform the minimal invasive surgery.

For this, the rotational insertion unit 320 may insert the arc-shaped rod 500 into each of the plurality of detachable parts 120 as illustrated in FIG. 18 in a state in which the handle 326 for the manual insertion is detachably coupled to the connection end with the connection bracket 323 in the insertion guide body 324 as illustrated in FIG. 17 so that the operator directly grapes and inserts the rod.

As described above, the technical ideas of the present disclosure is to provide the screw reducer for the minimal invasive surgery, which reduces the screw that is disposed at a height misaligned with the radius of the lordosis defined by the lumbar of the vertebrae of the subject person to help generation of the radius of the lordosis and the apparatus for the minimal invasive surgery using the same.

According to the foregoing embodiments, the following effects may be attained.

First, according to the embodiments, since the arc-shaped rod having various lengths and radii, which are required for the minimal invasive surgery in various cases, varies according to the lengths of the rotational support unit and the rotational insertion part and the increase or decrease of the level number through the structure in which the rotational insertion unit is rotatable with respect to the rotational support unit, the operation for easily and quickly penetrating and inserting the rod as one device into the plurality of screws to fix the rod may be performed.

For this, in the n-level (where n is an integer equal to or greater than 1) that is in a state in which the n+1 pedicle screws are respectively fixed to the n+1 vertebrae, the rotational support unit and the rotational insertion unit may be freely adjusted in length to correspond to the radius of the lordosis of the subject person according to the increase or decrease of the n number by the first adjusting part disposed on the rotational support unit and the second adjusting part disposed on the rotational insertion unit and thus may be very superior in view of versatility.

Also, according to the embodiments, the following effects may be attained.

First, even in case of a relatively large number of vertebrae, for example, the 3-level or more, each of the head parts of the above-described screws respectively fixed to the vertebrae may be quickly and easily fixed at a time by using one rod having the arc shape corresponding to the lordosis of the subject person through the structure in which the detachable part is rotatably coupled to the holder body having both penetrated ends.

Here, the holder body may include the stepped part that is disposed to be stopped on the upper portion of the support part, the screw thread disposed on the stepped part, and the alignment contact surface disposed on both sides of the outer circumference of the stepped part, and the alignment nut coupled to the screw thread. Thus, since the upper portions of the plurality of holder bodies having the above-described structure are aligned in the straight line by using one alignment unit, the detachable part rotatably coupled to each of the lower holder bodies may be maintained in the state in which the detachable part is accurately coupled to the head part of the screw, and the aligned state for the insertion of the rod may be easily and smoothly formed.

For this, although the number of holder bodies respectively coupled to the head parts of the screws having the 3-level or more are large according to the length of the clamping bar extending from the pair of grip parts that are rotatable with respect to the clamping axis, the alignment unit may sufficiently correspond to be maintained in the fixed state thereof so as to perform the operation.

Particularly, to insert one rod having the arc shape corresponding to the radius of the lordosis formed by the lumbar of the vertebrae of the subject person into the detachable part coupled to each of the holder units having the 3-level or more, which are aligned by the alignment unit, the above-described one rod may be accurately and quickly penetrated and inserted to be fixed by the rotatable insertion unit that is detachable from the alignment unit.

Also, according to the embodiments, the following effects may be attained.

First, according to the embodiments, the rod may be smoothly inserted before the rod is inserted, and the formation of the adequate radius of the lordosis may be helped through the structure including the corrector for forming the arc shape corresponding to the radius of the lordosis by reducing the screw disposed at the height misaligned with the radius of the lordosis.

Here, according to the embodiments, the outer surface of the alignment nut may be hooked and fixed to the hook protrusion disposed upward from the lower end of the inner surface of the correction body, and the screw disposed at the misaligned height may be reduced in place by the rotation of the correction body coupled to the alignment nut in the state in which the plurality of holder units are aligned with each other in the straight line. Thus, the operator may intuitively grasp regardless of the skill level to easily and quickly reduce the screw.

Although an exemplary embodiment of the present disclosure has been shown and described, it should be apparent to those having ordinary skill in the art that various changes, modifications, or alterations to the invention as described herein may be made, none of which change the spirit of the present disclosure. All changes, modifications, or alterations should therefore be seen as within the scope of the invention. Therefore, these combinations and modifications should be construed as falling within the scope of the present invention.

What is claimed is:

1. A rod inserter for fixing a pedicle screw, the rod inserter comprising:
    a rotational support unit having a length corresponding to a radius of lordosis formed by lumbar of vertebrae of a subject person, and having a lower end fixed; and
    a rotational insertion unit having a length corresponding to the radius and having one end rotatably coupled to an upper end of the rotational support unit and another end to which an arc-shaped rod is detachably coupled,
    wherein the length of the rotational support unit and the length of the rotational insertion unit vary according to an increase or decrease of an n number in an n-level, where n is an integer equal to or greater than 1, wherein the n-level is a state in which n+1 screws are configured to be respectively fixed to n+1 vertebrae, and
    wherein the rotational support unit comprises:
    a support cylinder of which a lower end is fixed;
    an accessible rod configured to be accommodated within the support cylinder;
    a rotational bracket disposed on an upper end of the accessible rod and to which an upper end of the rotational insertion unit is rotatably coupled; and
    a first adjusting part disposed on a connection portion of the support cylinder and the accessible rod to maintain a state in which the accessible rod is withdrawn or accommodated through the support cylinder.

2. The rod inserter of claim 1, wherein the rotational insertion unit comprises:
    a rotational bar rotatably coupled to the upper end of the rotational support unit;
    an accessible cylinder coupled to an end of the rotational bar to accommodate the rotational bar so that the rotational bar is accessible through the accessible cylinder, wherein a total length of the accessible cylinder and the rotational bar varies;
    a connection bracket extending from an end of the accessible cylinder to form a portion of the arc-shaped rod;
    an insertion guide body detachably coupled to the connection bracket to form the rest portion of the arc-shaped rod; and
    a second adjusting part disposed on a connection portion of the rotational bar and the accessible cylinder to maintain a state in which the rotational bar is withdrawn or accommodated through the accessible cylinder,
    wherein the arc-shaped rod is detachably coupled to an end of the insertion guide body, and
    the connection bracket, the insertion guide body, and the arc-shaped rod form an arc corresponding to the radius of the lordosis.

3. The rod inserter of claim 1, wherein the first adjusting part comprises:
    a first operation housing disposed on an upper end of the support cylinder to define an operation space therein;
    a first adjusting body disposed in the first operation housing, having one end exposed from an outer surface of the first operation housing, through which the accessible rod passes, wherein the first adjusting body reciprocates in a direction perpendicular to an accessible direction of the accessible rod;

a first biasing unit disposed between another end of the first adjusting body and an inner surface of the first operation housing to generate supporting force in a direction in which the first adjusting body protrudes to an outside of the first operation housing;

a first operation control unit disposed respectively on the support cylinder, an outer circumferential surface of the accessible rod, and the first adjusting body, the first operation control unit being engaged with or released from the accessible rod upon reciprocation of the first adjusting body to allow or restrict the accessible rod to be withdrawn from or to be accommodated within the support cylinder.

4. The rod inserter of claim 3, wherein the first adjusting body comprises:

a first reciprocation piece through which the accessible rod passes, wherein the first reciprocation piece reciprocates within the first operation housing;

a first pushing piece extending from one end of the first reciprocation piece and exposed from a first access slot passing through an outer surface of the first operation housing, wherein the first biasing means is disposed between another end of the first reciprocation piece and an inner surface of the first operation housing, and a portion of the first operation control unit is disposed on the first reciprocation piece.

5. The rod inserter of claim 2, wherein the second adjusting part comprises:

a second operation housing disposed on an upper end of the accessible cylinder to define an operation space therein;

a second adjusting body disposed in the second operation housing, having one end exposed from an outer surface of the second operation housing, through which the rotational bar passes, wherein the second adjusting body reciprocates in a direction perpendicular to an accessible direction of the rotational bar;

a second biasing unit disposed between another end of the second adjusting body and an inner surface of the second operation housing to generate supporting force in a direction in which the second adjusting body protrudes to an outside of the second operation housing;

a second operation control unit disposed respectively on the accessible cylinder, an outer circumferential surface of the rotational bar, and the second adjusting body, the second operation control unit being engaged with or released from the rotational bar upon reciprocation of the second adjusting body to allow or restrict the rotational bar to be withdrawn from or to be accommodated within the accessible cylinder.

6. The rod inserter of claim 5, wherein the second adjusting body comprises:

a second reciprocation piece through which the rotation bar passes, wherein the second reciprocation piece reciprocates within the second operation housing;

a second pushing piece extending from one end of the second reciprocation piece and exposed from a second access slot passing through an outer surface of the second operation housing, wherein the second biasing unit is disposed between another end of the second reciprocation piece and an inner surface of the second operation housing, and a portion of the second operation control unit is disposed on the second reciprocation piece.

* * * * *